(12) United States Patent
Dastgir et al.

(10) Patent No.: US 11,312,677 B2
(45) Date of Patent: Apr. 26, 2022

(54) SYNTHESIS OF BUILDING BLOCKS AND FEEDSTOCKS FOR MANUFACTURING RENEWABLE POLYMERS

(71) Applicant: Qatar Foundation for Education, Science and Community Development, Doha (QA)

(72) Inventors: Sarim Dastgir, Doha (QA); Francesco Ferretti, Doha (QA); Muhammad Sharif, Doha (QA); Ralf Jackstell, Doha (QA); Matthias Beller, Doha (QA); Douglas W. Stephan, Doha (QA); Louie Fan, Doha (QA)

(73) Assignee: QATAR FOUNDATION FOR EDUCATION, SCIENCE AND COMMUNITY DEVELOPMENT, Doha (QA)

( * ) Notice: Subject to any disclaimer, the term of this patent is extended or adjusted under 35 U.S.C. 154(b) by 138 days.

(21) Appl. No.: 16/621,555

(22) PCT Filed: Jun. 7, 2018

(86) PCT No.: PCT/QA2018/050003
§ 371 (c)(1),
(2) Date: Dec. 11, 2019

(87) PCT Pub. No.: WO2018/231082
PCT Pub. Date: Dec. 20, 2018

(65) Prior Publication Data

US 2021/0292266 A1    Sep. 23, 2021

Related U.S. Application Data

(60) Provisional application No. 62/518,400, filed on Jun. 12, 2017.

(51) Int. Cl.
| | | |
|---|---|---|
| *C07C 51/09* | (2006.01) | |
| *C07C 29/00* | (2006.01) | |
| *C07C 29/149* | (2006.01) | |
| *B01J 23/44* | (2006.01) | |

(52) U.S. Cl.
CPC ............ *C07C 51/09* (2013.01); *C07C 29/149* (2013.01); *B01J 23/44* (2013.01)

(58) Field of Classification Search
CPC .............................. C07C 51/09; C07C 29/149
See application file for complete search history.

(56) References Cited

U.S. PATENT DOCUMENTS

| | | |
|---|---|---|
| 2003/0176737 A1 | 9/2003 | Behr et al. |
| 2014/0194648 A1 | 7/2014 | Boeing et al. |

FOREIGN PATENT DOCUMENTS

| | | |
|---|---|---|
| CN | 105622560 A | 6/2016 |
| RU | 2217428 C2 | 11/2003 |
| WO | 2017202644 A1 | 11/2017 |

OTHER PUBLICATIONS

International Search Report for related International Application No. PCT/QA/2018/050003; report dated May 28, 2020; (2 pages).
Written Opinion for related International Application No. PCT/QA/2018/050003; report dated May 28, 2020; (3 pages).
International Preliminary Report on Patentability for related International Application No. PCT/QA/2018/050003; report dated Jun. 2, 2020; (4 pages).
Behr et al., Aqueous biphasic catalysis as a powerful tool for catalyst recycling in telomerization and hydrogenation chemistry. Green Chemistry, vol. 5, Feb. 28, 2003, pp. 198-204.
Behr et al., Bimetallic-Catalyzed Reduction of Carboxylic Acids and Lactones to Alcohols and Diols, Adv. Synth. Catal., vol. 344, No. 5, 2002, pp. 525-532.
Ferretti et al., Selective palladium-catalysed synthesis of diesters: alkoxycarbonylation of a CO2-butadiene derived 6-lactone, Green Chemistry, vol. 19, Jun. 26, 2017 (retrieved on Apr. 24, 2020]. Retrieved from the Internet: <URL: https://pubs.rsc.org/en/content/articlelanding/2017/gc/c7gc01366c#!divAbstract>. see Abstract.
Office Action for related Russian Application No. 2020100077; action dated Oct. 8, 2021; (16 pages).
Search Report for related Russian Application No. 2020100077; action dated Oct. 8, 2021; (4 pages).

*Primary Examiner* — Sikarl A Witherspoon
(74) *Attorney, Agent, or Firm* — K&L Gates LLP

(57) ABSTRACT

Disclosed are methods or processes of synthesizing building blocks and feedstocks for producing a broader range of polymers, including renewable polymers, from renewable resources such as $CO_2$. In a process of manufacturing a renewable feedstock for polymer production, a $CO_2$ derived lactone is prepared and processed to form the renewable feedstock. The process may include alkoxycarbonylation of the $CO_2$ derived lactone to form a diester and hydrogenation of the diester.

19 Claims, 8 Drawing Sheets

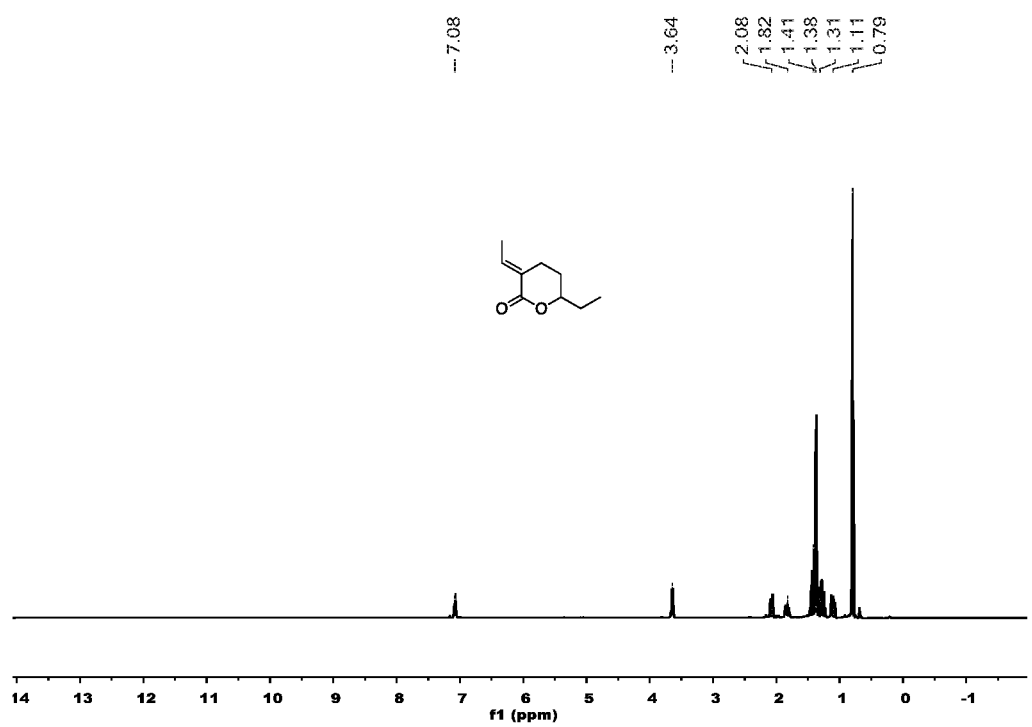
FIGURE 1: ¹H NMR (400 MHz, C₆D₆) of hydrogenated δ-lactone 1

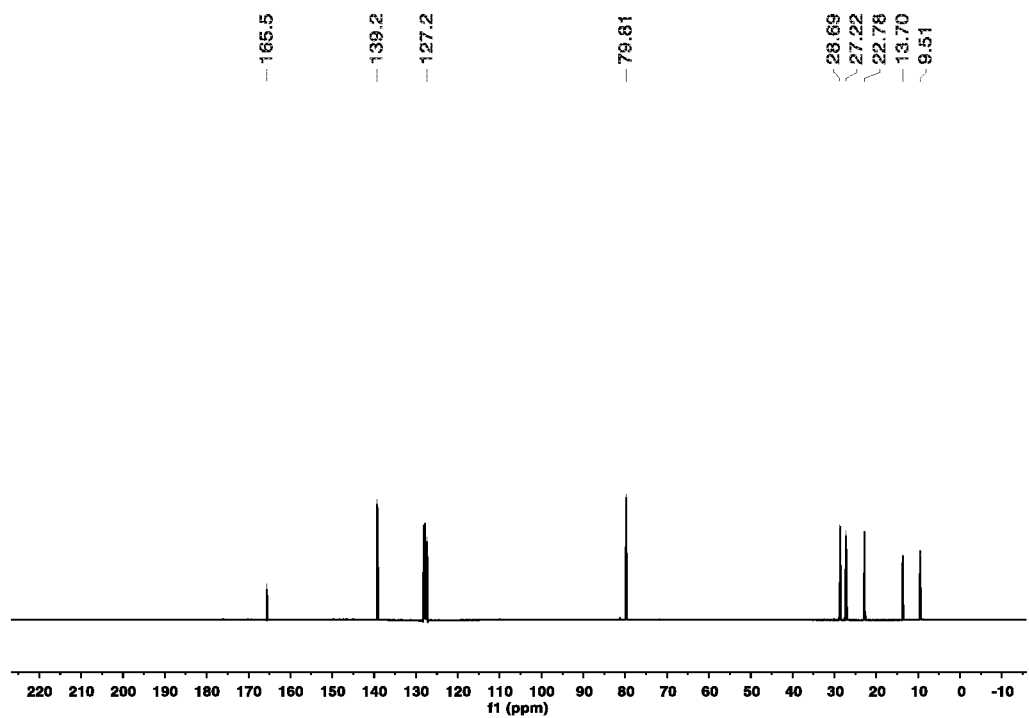
FIGURE 2: $^{13}$C NMR (125 MHz, C$_6$D$_6$) of hydrogenated δ-lactone 1

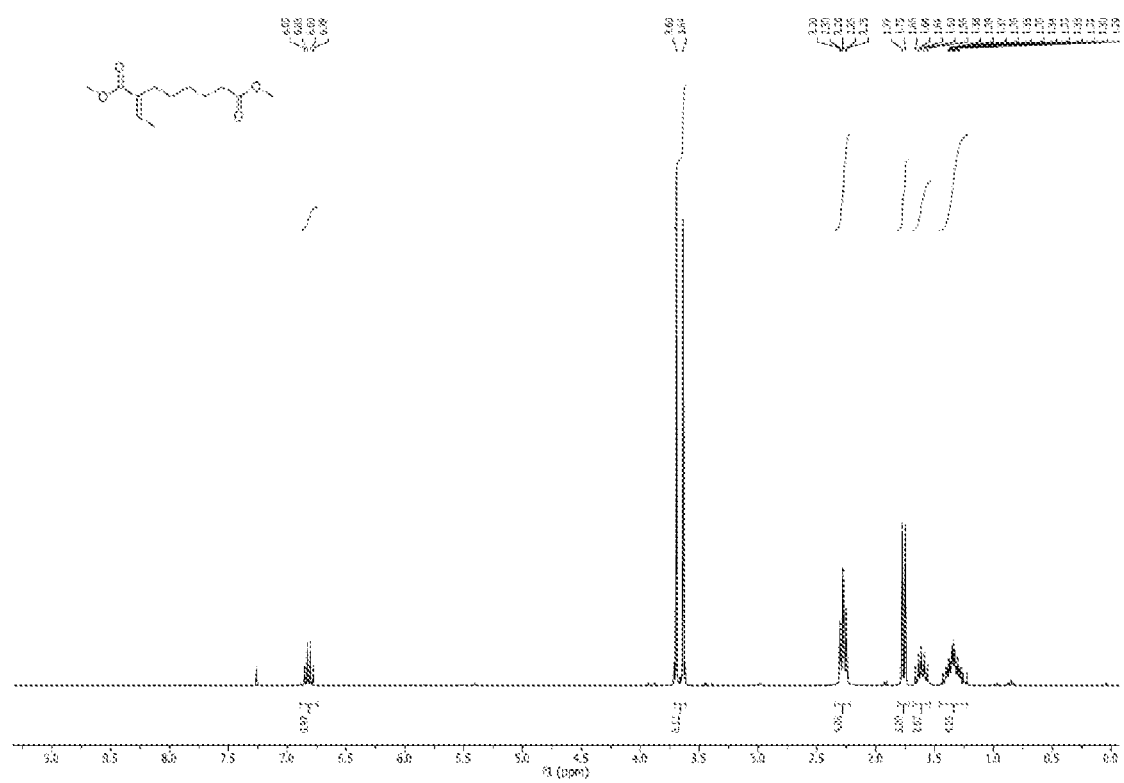
FIGURE 3: $^1$H NMR (300 MHz, CDCl$_3$) of dimethyl 2-ethylideneoctanedioate 3: δ 6.82 (q, $J$ = 7.1 Hz, 1H), 3.69 (s, 3H), 3.64 (s, 3H), 2.38 – 2.18 (m, 4H), 1.76 (d, $J$ = 7.1 Hz, 3H), 1.67 – 1.55 (m, 2H), 1.45 – 1.20 ppm (m, 4H).

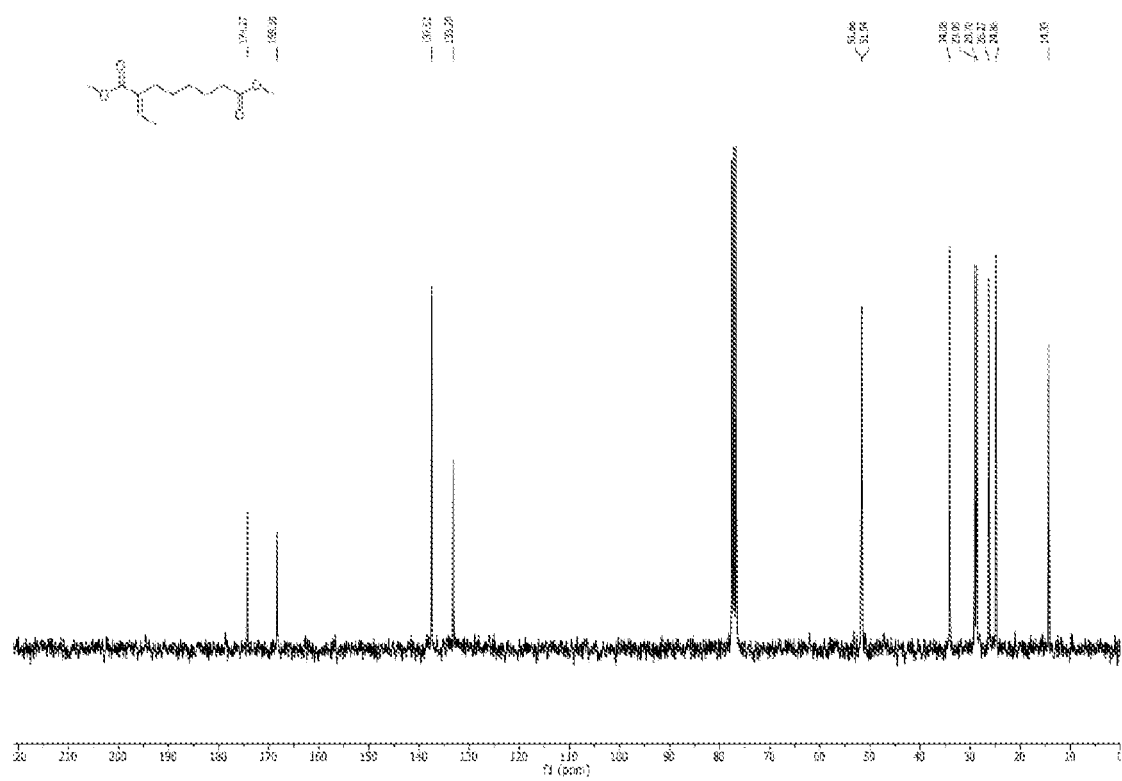
FIGURE 4: $^{13}$C NMR (75 MHz, CDCl$_3$) of dimethyl 2-ethylideneoctanedioate 3: δ 174.3, 168.4, 137.5, 133.2, 51.7, 51.5, 34.1, 29.1, 28.7, 26.3, 24.9, 14.3.ppm.

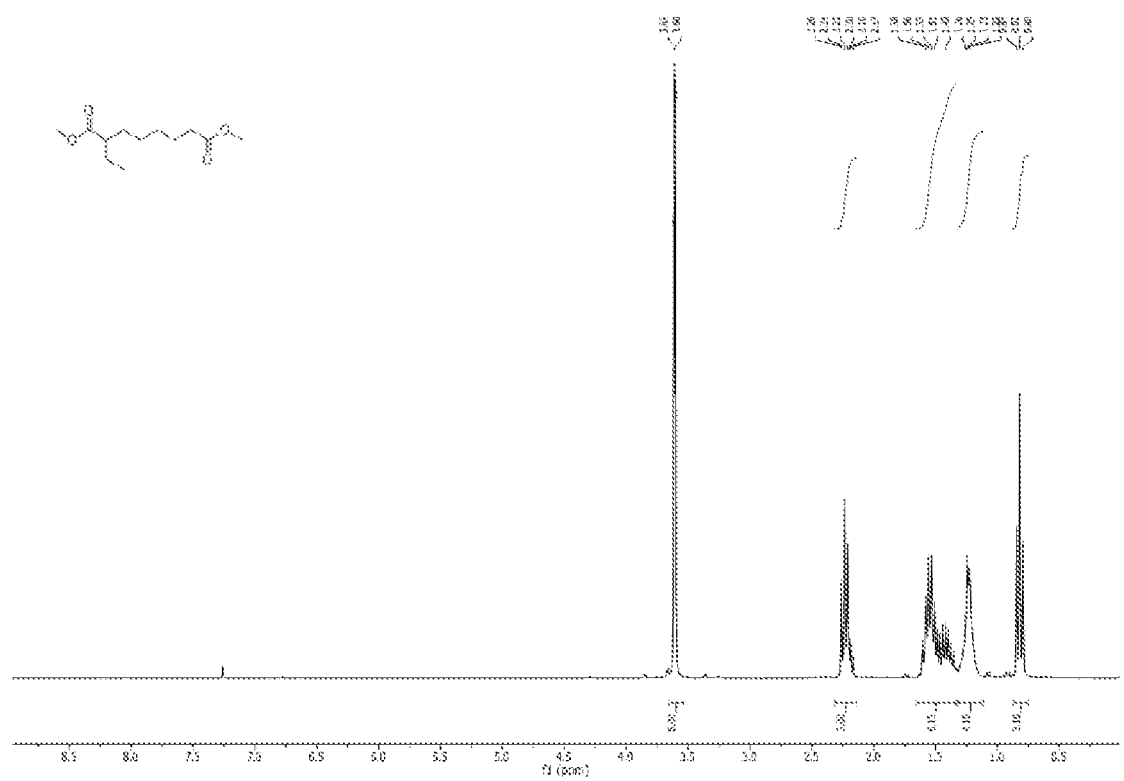
FIGURE 5: ¹H NMR (300 MHz, CDCl₃) of dimethyl 2-ethyloctanedioate 4: δ 3.61 (s, 3H), 3.60 (s, 3H), 2.32 – 2.14 (m, 3H), 1.49 (m, 6H), 1.32 – 1.12 (m, 4H), 0.82 ppm (t, $J$ = 7.4 Hz, 3H).

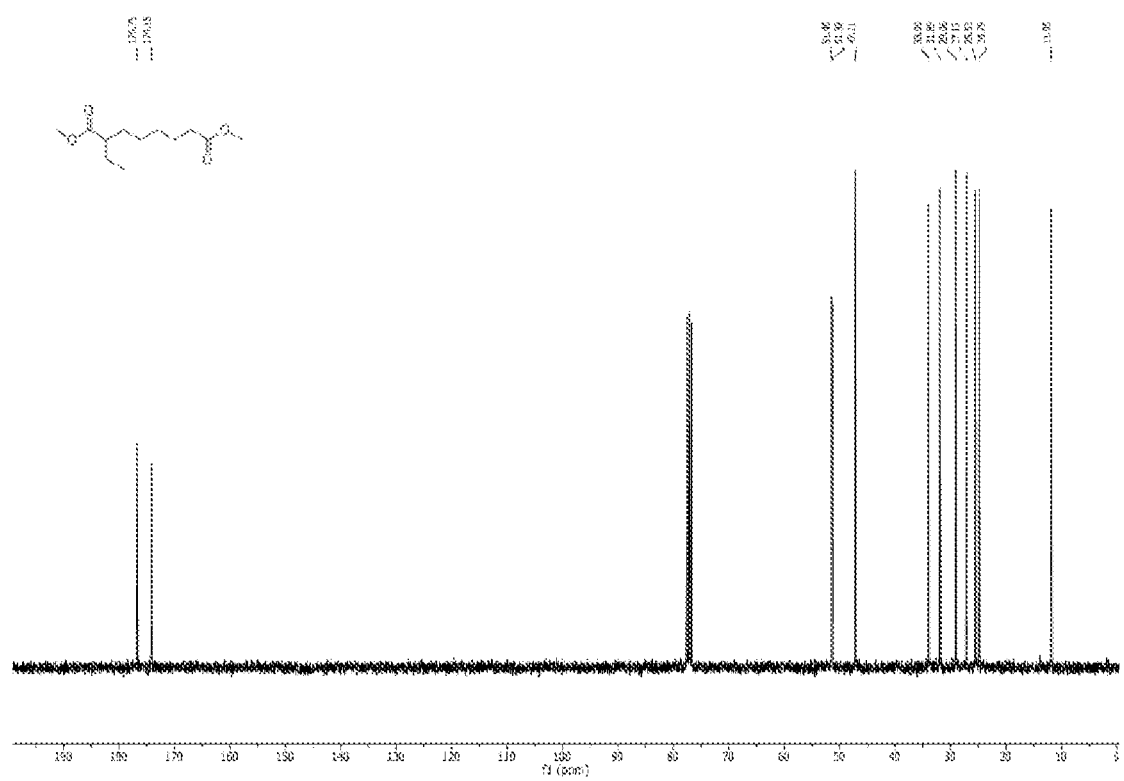
FIGURE 6: $^{13}$C NMR (75 MHz, CDCl$_3$) of dimethyl 2-ethyloctanedioate 4: δ 176.7, 174.1, 51.5, 51.3, 47.2, 34.0, 31.9, 29.1, 27.1, 25.5, 24.8, 11.8 ppm.

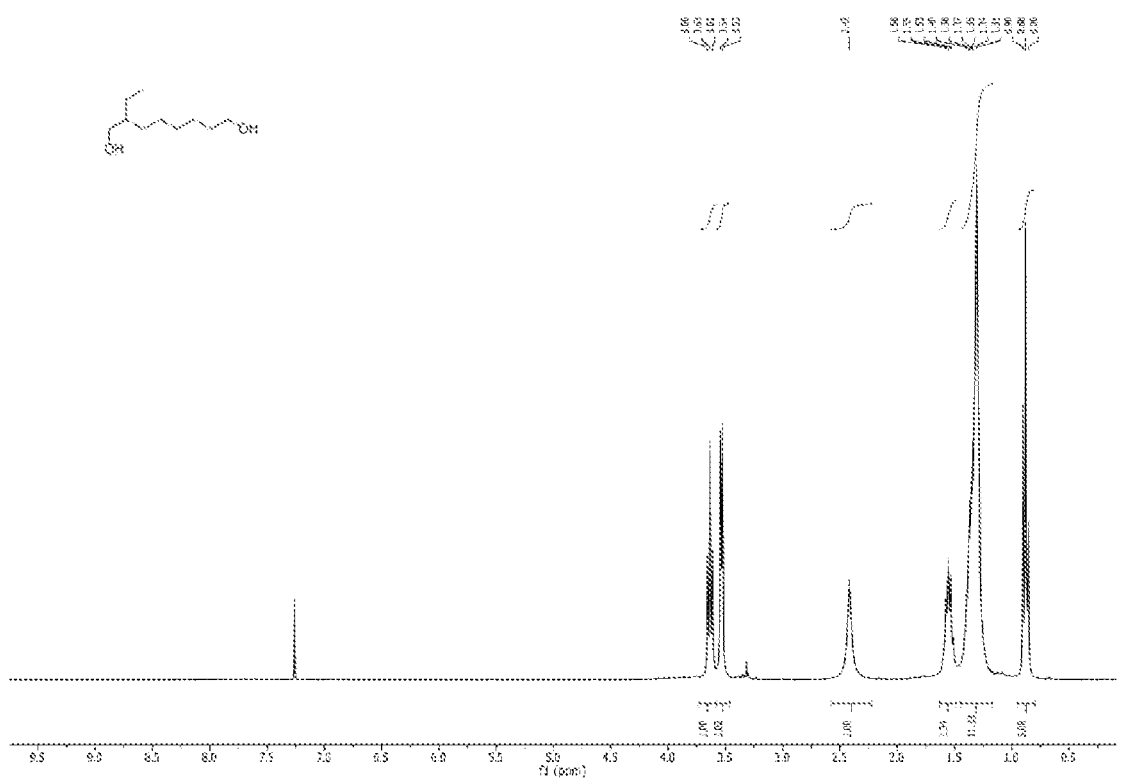
FIGURE 7: $^1$H NMR (300 MHz, CDCl$_3$) of 2-ethyloctane-1,8-diol 5: δ 3.63 (t, $J$ = 6.6 Hz, 2H), 3.53 (d, $J$ = 5.0 Hz, 2H), 2.42 (br s, 2H), 1.70 – 1.47 (m, 2H), 1.44 – 1.15 (m, 11H), 0.88 ppm (t, $J$ = 7.3 Hz, 3H).

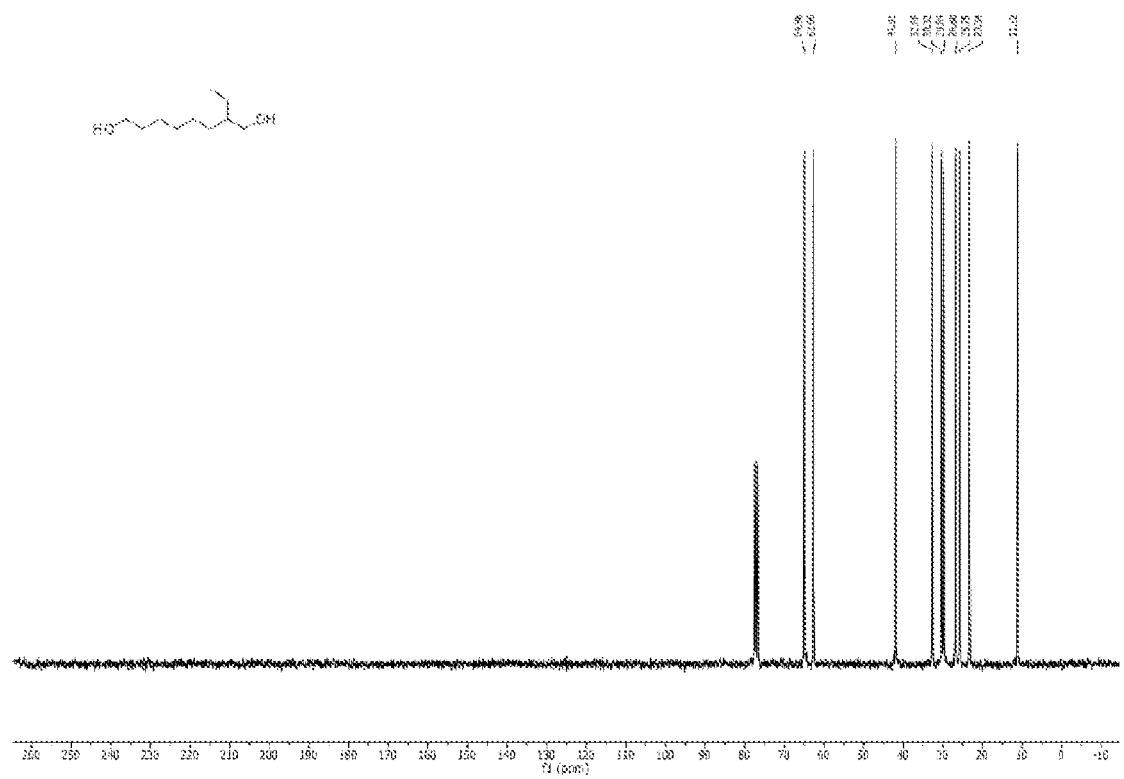
FIGURE 8: $^{13}$C NMR (75 MHz, CDCl$_3$) of 2-ethyloctane-1,8-diol 5: δ 65.0, 62.7, 41.9, 32.7, 30.3, 29.8, 26.8, 25.7, 23.3, 11.1.

SYNTHESIS OF BUILDING BLOCKS AND FEEDSTOCKS FOR MANUFACTURING RENEWABLE POLYMERS

CROSS REFERENCES TO RELATED APPLICATIONS

The present application is a National Stage filing under 35 U.S.C. 371 of International Application No. PCT/QA2018/050003, filed on Jun. 7, 2018 which claims priority to provisional Patent Application No. 62/518,400 filed on Jun. 12, 2017, the disclosure of which is incorporated herein by reference.

BACKGROUND

One of the most important tasks for 21$^{st}$ century scientists is to provide practical ways to substitute fossil-based feedstocks by renewables. In this context, an important challenge for organic chemistry and the chemical industry is the effective use of carbon dioxide. Indeed, this area is of actual interest, and many efforts have been spent in the past decades to develop synthetic methodologies employing $CO_2$ as a raw material. Clearly, one promising way of using $CO_2$ is its inclusion into polymers. As an example, processes based on the reaction of $CO_2$ and epoxides to produce polycarbonates and polyethercarbonates have been commercialized in recent years. So far, they remain the only polymers that include $CO_2$ of practical and commercial interest.

SUMMARY

The inventors have recognized the need for methods or processes of synthesizing building blocks and feedstocks for producing a broader range of polymers, including renewable polymers, from renewable resources such as $CO_2$.

In one embodiment, a process of manufacturing a renewable feedstock for polymer production comprises preparing a $CO_2$ derived lactone and processing the $CO_2$ derived lactone to form the renewable feedstock. In one embodiment, processing the $CO_2$ derived lactone comprises hydrogenating the $CO_2$ derived lactone to form a hydrogenated $CO_2$ derived lactone.

In one embodiment, a process of manufacturing a renewable feedstock for polymer production comprises preparing a $CO_2$ derived lactone and alkoxycarbonylating the $CO_2$ derived lactone to form a diester. In one embodiment, the process further comprises hydrogenating the diester to form the renewable feedstock.

BRIEF DESCRIPTION OF DRAWINGS

FIG. 1 shows $^1$H NMR (400 MHz, $C_6D_6$) of δ-lactone 1.
FIG. 2 shows $^{13}$C NMR (125 MHz, $C_6D_6$) of δ-lactone 1.
FIG. 3 shows $^1$H NMR (300 MHz, $CDCl_3$) of dimethyl 2-ethylideneoctanedioate 3.
FIG. 4 shows $^{13}$C NMR (75 MHz, $CDCl_3$) of dimethyl 2-ethylideneoctanedioate 3.
FIG. 5 shows $^1$H NMR (300 MHz, $CDCl_3$) of dimethyl 2-ethyloctanedioate 4.
FIG. 6 shows $^{13}$C NMR (75 MHz, $CDCl_3$) of dimethyl 2-ethyloctanedioate 4.
FIG. 7 shows $^1$H NMR (300 MHz, $CDCl_3$) of 2-ethyloctane-1,8-diol 5.
FIG. 8 shows $^{13}$C NMR (75 MHz, $CDCl_3$) of 2-ethyloctane-1,8-diol 5.

DETAILED DESCRIPTION

The present disclosure provides methods or processes of synthesizing building blocks and feedstocks for producing a broader range of polymers, including renewable polymers, from renewable resources such as $CO_2$. For example, the inventors have surprisingly discovered a successful catalytic system for the alkoxycarbonylation of δ-lactone 1 derived from the telomerization of $CO_2$ and butadiene and further synthesis of valuable unsaturated diesters 2 from $CO_2$ derived δ-lactone 1. The inventors have developed a high yielding one pot procedure for the synthesis of $C_{10}$ unsaturated diesters from such δ-lactone according to an embodiment. The inventors have also investigated the catalytic hydrogenation of such obtained diesters to their saturated form and to diol, where the diesters and diol derived from the reaction are relevant building blocks for the synthesis of polyesters according to an embodiment. A regioselective hydrogenation of δ-lactone 1 with the retention of the lactone ring structure and synthesis of valuable polymer building blocks therefrom is further provided according to an embodiment. The following provides further description of the present disclosure according to an embodiment.

Synthesis of $CO_2$ Derived δ-Lactone

The synthesis of polymers or monomers derived from the reaction between $CO_2$ and olefins allows the preparation of $CO_2$-based materials with different physical and mechanical properties. Although different olefins are known to react with carbon dioxide in the presence of specific metal complexes, in nearly all cases the release of the olefin-$CO_2$ adduct requires additional stoichiometric reagents leading to large amount of waste. Thus, direct olefin/$CO_2$ polymerization or the synthesis of monomers derived from them in a sustainable and economical way is a very difficult task.

An exception to the above described reactivity is the catalytic telomerisation reaction of 1,3-dienes with carbon dioxide. Using a tertiary mono-phosphine and a Pd(0) precursor, δ-lactone (3-ethylidene-6-vinyltetrahydro-2H-pyran-2-one) can be obtained with good selectivity (Scheme 1). A primary source of 1,3-butadiene is as a by-product of steam cracking process of ethylene and can also be produced from renewable feedstocks.

Scheme 1: Synthesis of δ-lactone 1 by telomerization of butadiene and $CO_2$

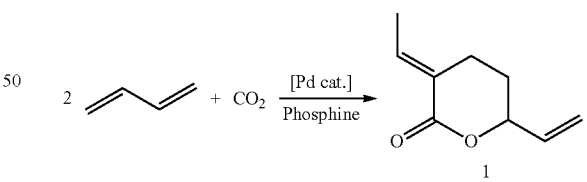

Regioselective Hydrogenation of δ-Lactone and Synthesis of Polymer Building Blocks Therefrom Further, a regioselective hydrogenation of δ-lactone 1 with the retention of lactone ring structure is described. The following describes examples and embodiments directed to such a regioselective hydrogenation of δ-lactone 1 and synthesis of valuable polymer building blocks therefrom.

In some embodiments, δ-lactone 1 can be selectively hydrogenated with 100% region-selective control for the terminal carbon-carbon bonds. Such a regioselective hydrogenation for δ-lactone 1 is unprecedented with the retentions of lactone ring structure.

In some embodiments, such reactions are performed under an atmosphere of dry, oxygen-free, nitrogen-filled glove box (Innovative Technology). In some embodiments, the solvents (including deuterated) are dried and stored over molecular sieves (4 Å pellets, 3.2 mm diameter) under a nitrogen atmosphere before use. $B(C_6F_5)_3$ was commercially available from Boulder Scientific Chemicals. In some embodiments, the $H_2$ (grade 5.0) is purchased from Linde and dried through a Nanochem Weldassure purifier column prior to use. In some embodiments, the nuclear magnetic resonance (NMR) spectroscopy spectra are recorded on a Bruker Avance III 400 MHz or Agilent DD2 500 MHz spectrometer. In some embodiments, a Perkin-Elmer analyzer is used for carbon, hydrogen, and nitrogen elemental analysis.

In some embodiments, in a glovebox, compound 1 (219 mg, 1.44 mmol) is weighed into 2 dram vial. $B(C_6F_5)_3$ (36.8 mg, 0.072 mmol) dissolved in 3 mL of diethyl ether is added to the vial. In some embodiments, the reaction vessel is equipped with a stirbar, loosely capped and placed inside a Parr pressure reactor. In some embodiments, the reactor is purged ten times at 15 atm with hydrogen gas. The reactor is sealed, removed from the glove box and attached to a purged hydrogen gas line. The reactor is then pressurized with 60 atm hydrogen gas and placed in an oil bath for 12 h at 70° C. and 540 rpm. The reactor is slowly vented and the mixture is filtered through a plug of silica, and volatiles are removed in a vacuum. The NMR of the crude sample, FIGS. 1-2, shows complete regioselective conversion of the starting lactone 1 to lactone 1a (Scheme 2).

Scheme 2: Complete regioselective conversion of the starting lactone 1 to lactone 1a

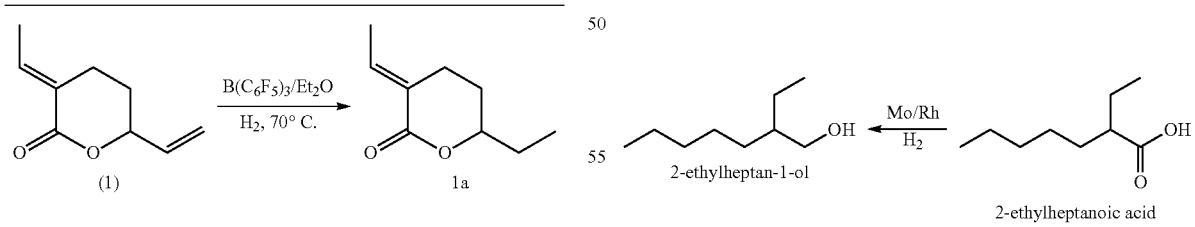

The partially hydrogenated δ-lactone can be transformed to C8 to C14-Building Blocks, Carbonyl Compounds, esters, amino building blocks, Chemical reagent, Polyols, Esters, Organic Building Blocks, monomers, food additives, Graft Co-polymerisation, Dendrimers, Coating for Biomedical Devices, Polyurethane building blocks.

For example, the hydrogenated δ-lactone can be transformed to 2-ethylideneheptanoic acid using homogeneous and/or heterogeneous hydrogenation system (Scheme 3). Similar reactions using Rh/phosphine biphasic hydrogenation systems can obtain opening of the ring structure in more than 92% overall yield with formation of multiple isomers.

Scheme 3: Hydrogenation of δ-lactone

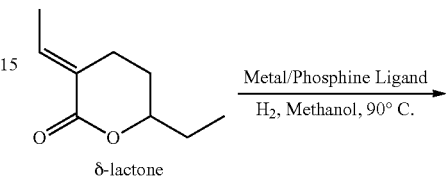

δ-lactone (Z)-2-ethylideneheptanoic acid $H_2$ | Pd/C

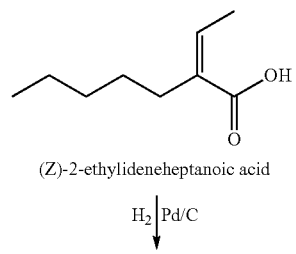

2-ethylheptan-1-ol 2-ethylheptanoic acid

The hydrogenated δ-lactone can be transformed to building block molecules and polymers using amination and Hydroaminomethylation methodologies. The hydrogenated δ-lactone can be regioselectively polymerised using the retention and/or cleavage of the ring structure.

The hydrogenated δ-lactone can be regioselectively polymerised using thiol click reaction (Thiol-Michael Addition) to produce regioselective polymers with tailored properties (Scheme 4). The thiol co-monomer can be taken from a group of an appropriate with one, two, three and/or four —SH containing monomers.

Scheme 4: Co-polymerization of hydrogenated δ-lactone via Thiol-Michael Addition Reaction

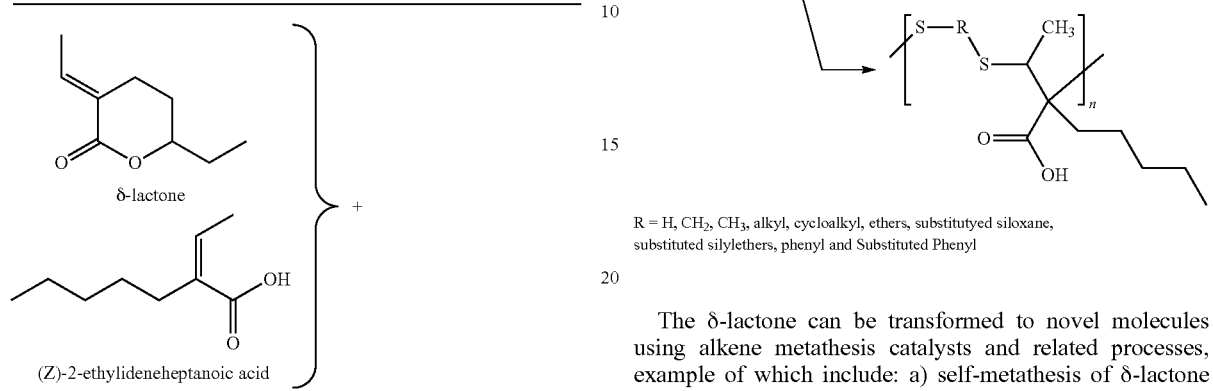

R = H, CH$_2$, CH$_3$, alkyl, cycloalkyl, ethers, substitutyed siloxane, substituted silylethers, phenyl and Substituted Phenyl The δ-lactone can be transformed to novel molecules using alkene metathesis catalysts and related processes, example of which include: a) self-metathesis of δ-lactone (Scheme 5) and b) cross metathesis of δ-lactone (Scheme 6) as shown below.

Scheme 5: Building blocks resulting from self-metathesis of δ-lactone

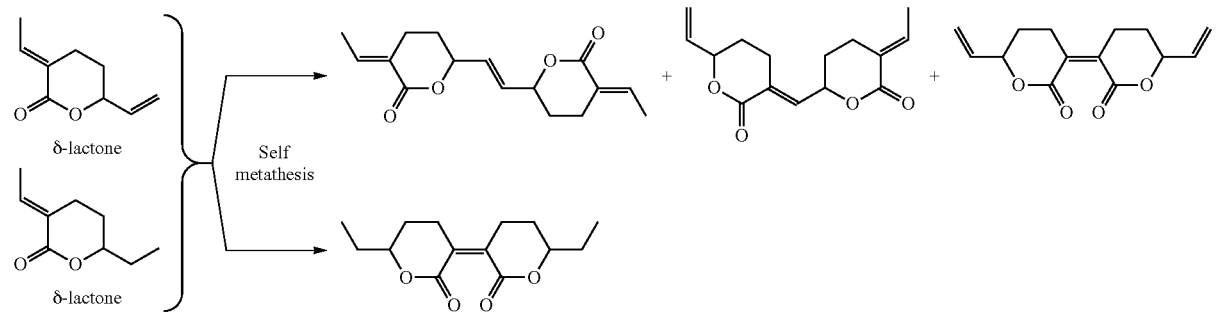

Scheme 6: Building blocks resulting from cross metathesis of δ-lactone

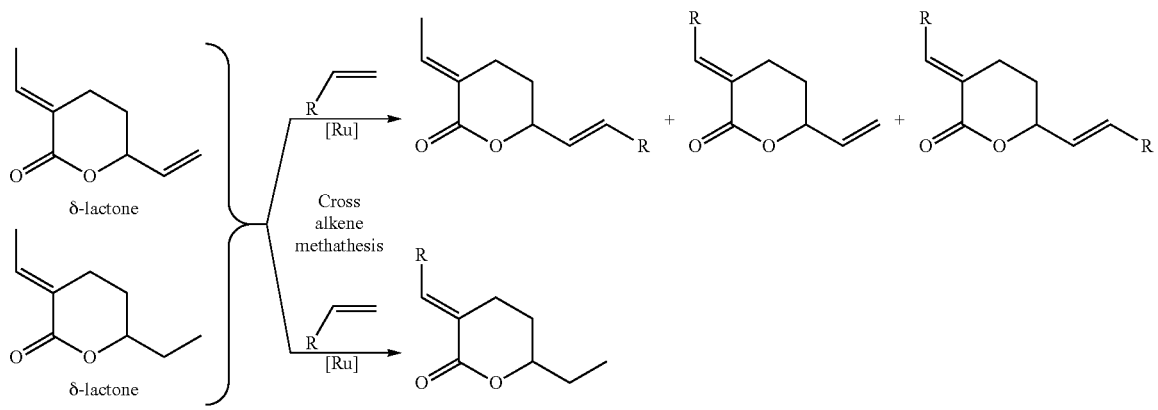

R = H, CH$_2$, CH$_3$, alkyl, cycloalkyl, lactone, phenyl and Substituted Phenyl The δ-lactone can be transformed to novel lactam molecules via metal catalysed transformation of lactones, examples of which are shown below in scheme 7.

general reactivity of δ-lactone with H-Y type substrates, such as water, alcohols, amines or silanes. It is not easy to suppress non-selective alcoholysis of δ-lactone. For

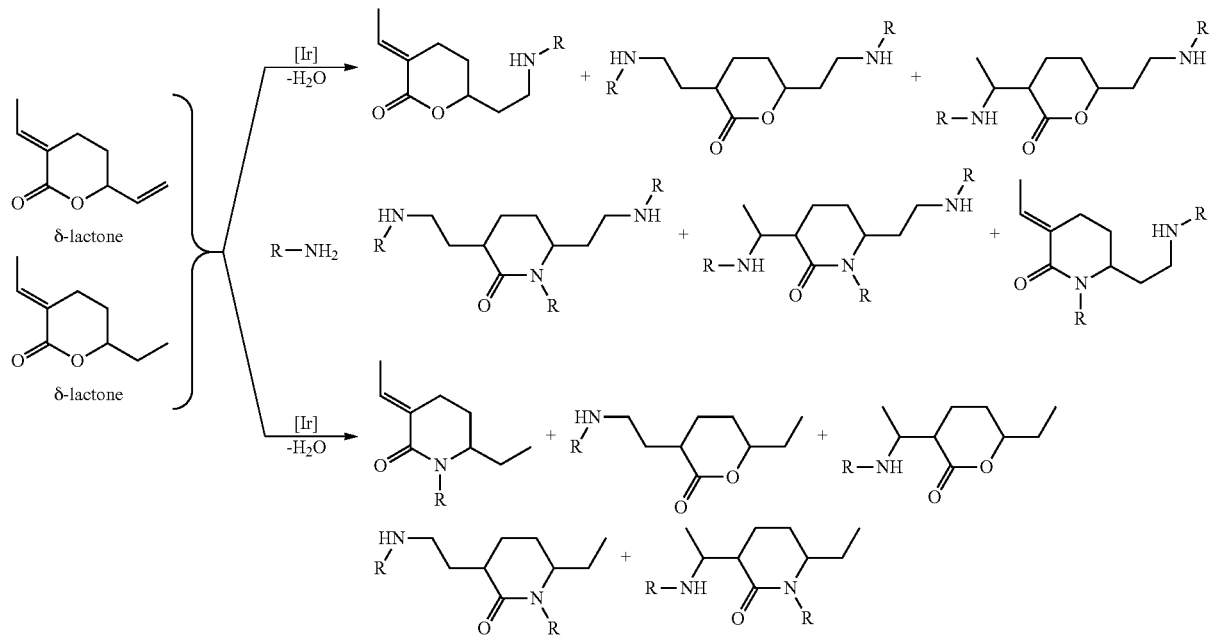

Scheme 7: Transition metal catalyzed transformation of δ-lactone to Lactam building blocks R = H, CH$_2$, CH$_3$, alkyl, cycloalkyl, ethers, substitutyed siloxane, substituted silylethers, phenyl and Substituted Phenyl Synthesis of Polymer Building Blocks from Alkoxycarbonylation of δ-Lactone and Hydrogenation of Products Thereof Further, straightforward valorization of δ-lactone to other monomers, polymers and plasticizers offers interesting possibilities for using $CO_2$. δ-lactone has been studied in a variety of reactions such as hydrogenation, hydroformylation, hydroaminometylation, hydroamination, alcoholysis and hydrolysis to produce carboxylic acids and esters, diols as well as functionalised lactones. Some of these compounds are of interest to produce polymers and polymer related materials. In particular, diols and hydroxy-carboxylic acids are potential monomers for polyester and polyurethane chemistry while both mono-carboxylic acid and alcohols can be used in plasticizers production. The synthesis of polymers either by δ-lactone polymerization or by one-pot/two-step co/terpolymerisation of carbon dioxide and 1,3-dienes via lactone intermediate has also been studied. The following describes examples and embodiments of synthesizing valuable building blocks from alkoxycarbonylation of δ-lactone and further hydrogenation of the products therefrom.

δ-lactone can undergo carbonylation reactions, and di- or tri-esters derived from carbonylation of δ-lactone result in building blocks that should be of high potential interest for the polymer industry. However, attempts of alkoxycarbonylation of δ-lactone using Pd(OAc)$_2$/triphenylphosphine as the catalyst and p-toluenesulfonic acid (PTSA) as promoter, unexpectedly, resulted only in its alcoholysis, but no carbonylation product.

Sometimes in catalytic hydroesterification reactions of olefins, the opening of the lactone to yield different esters may not be avoided without acidic promoter if a palladium/ phosphine catalyst is present. This may be because of the example, when δ-lactone is heated in toluene in the presence of a primary alcohol and an acid, alcoholysis to a mixture of non-cyclic isomeric products may take place in the absence of palladium.

The inventors have developed a straightforward procedure for the synthesis of diesters from selective alcoholysis of δ-lactone including the synthesis of valuable unsaturated diesters 2 from δ-lactone 1 as described below in further detail according to an embodiment. Key to success for the selective esterification/allylic substitution/alkoxycarbonylation domino sequence of δ-lactone 1 is the use of specific palladium catalysts based on PdCl$_2$ and chelating diphosphines substituted with electron-withdrawing groups. The resulting unsaturated diesters can be selectively hydrogenated under mild conditions to mono-unsaturated diesters or to saturated diesters, both of which are relevant building blocks for the synthesis of functional materials or plasticizers. Moreover, such diesters can be also hydrogenated to 2-ethyloctane-1,8-diol 5 that offers new possibilities for the synthesis of polymers. In general, the overall process constitutes a new way to building blocks from δ-lactone 1 derived from $CO_2$ and butadiene, thus a new step towards renewable polymers.

Conventionally, the synthesis of 2-ethylideneoctanedioic acid, an α,ω unsaturated diacid related to esters 7-ethylideneoct-3-enedioic acid 2, from δ-lactone requires a three steps procedure: an initial rhodium/phosphine catalyzed hydrogenolysis of δ-lactone to a mixture of isomeric unsaturated C$_9$-carboxylic acids followed by rhodium/phosphite catalysed isomerization/hydroformylation of one double bond with syngas and finally oxidation of the obtained aldehyde. However, the inventors surprisingly discovered a more efficient direct methoxycarbonylation process of δ-lactone to dimethyl 7-ethylideneoct-3-enedioate 2a (Scheme 8).

Scheme 8: Formation of esters of 7-ethylideneoct-3-enedioic acid 2 by alkoxycarbonylation of δ-lactone 1

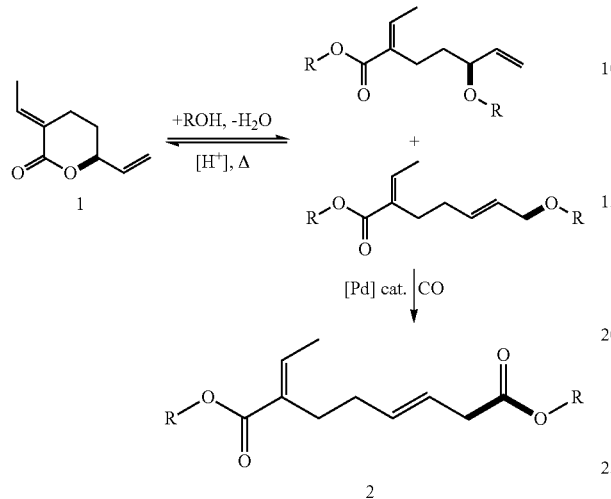

In some embodiments, catalytic hydroesterification reactions of δ-lactone are performed using a palladium compound (such as Pd(OAc)$_2$, PdCl$_2$, Pd(dba)$_2$) in combination with a mono- or diphosphine, an alcohol and/or an acidic promoter.

In some embodiments, the diester may be synthesized through a domino alcoholysis/allylic substitution/carbonylation reaction. In some embodiments, alcoholysis of δ-lactone and subsequent allylic substitution may yield a mixture of esters bearing an allylic ether moiety that can be carbonylated further on to the unsaturated diester.

Scheme 9: Palladium-catalyzed alkoxycarbonylation of the allylic position of δ-lactone 1. Investigation of different phosphine ligands.

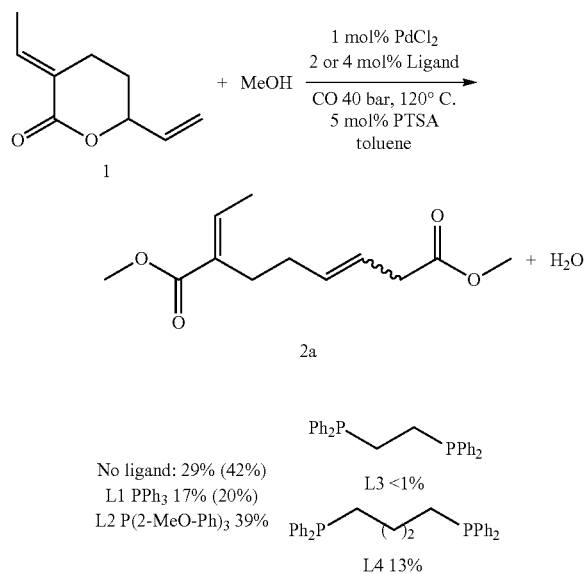

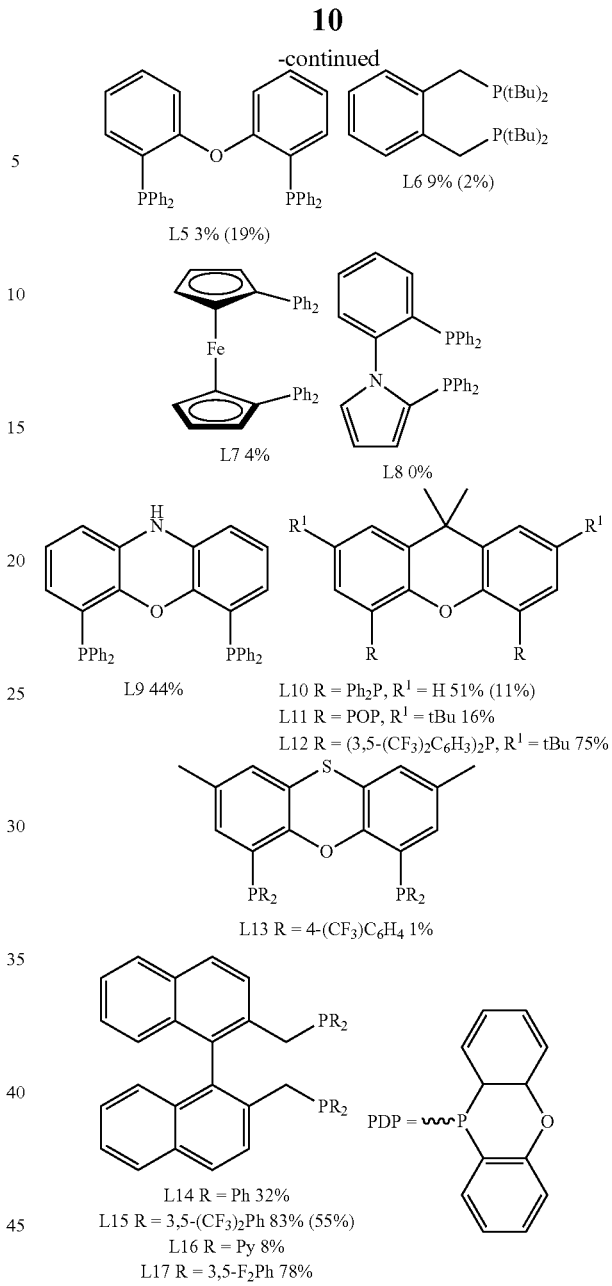

Reaction conditions: 1 (1.0 mmol), PdCl$_2$ (1 mol %), monodentate ligand (4 mol %) or bidentate ligand (2 mol %), PTSA (5 mol %) toluene (2 mL), MeOH (0.25 mL, 6 mmol). CO (40 bar), 120° for 5 h; yields determined by GC analysis using hexadecane as the internal standard; number in parenthesis indicates yield after 20 h. Yield is given as sum of E and Z isomers.

In some embodiments, different phosphines, for example, L1-L17 in Scheme 9, are used in combination with PdCl$_2$ as precatalyst and PTSA as acidic promoter. In some embodiments, the reaction takes place even in the absence of a phosphine. In some embodiments, metallic palladium may be present at the end, and therefore, a ligand may be needed to stabilize the catalytic system. In some embodiments, monodentate phosphines, such as (L1 and L2), resulted in 20%-39% yield of 2a, but only a small amount palladium black was detected at the end of the reaction.

In some embodiments, bisphosphines, such as L3-L8, resulted in 20%-39% yield of 2a. In some embodiments, the large bite-angle ligand Xantphos, such as L10, obtained 2a in a yield of 51%, when the reaction was performed for κ h.

In some embodiments, the 2a yield decreases upon prolonging the reaction time to 20 h, maybe due to further carbonylation of the double bonds of 2a. In some embodiments, phosphines of the Xantphos families, such as L9-L13, and of NaPhos families, such as L14-L17, are used. The ones substituted with electron-withdrawing groups, such as L12, L15 and L17, resulted in yields over 70%. IPhos, such as L15, resulted in a yield of 83% in a short reaction time. Notably, in this case, even prolonging the reaction to 20 h, the 2a yield did not decrease and can be 85%.

In some embodiments, the methoxycarbonylation of δ-lactone is conducted using L15 as ligand under different conditions. The conditions and results of some examples are shown in Table 1. In some examples, PTSA is used. For example, in entries 1-4 of Table 1, when the amount of PTSA from 1 mol % to 15 mol %, the yield of 2a first increases and reaches a plateau. In some examples, methanesulfonic acid (MSA) is used. For example, in entry 5, the yield is 84%. In some examples, hydrochloric acid is used. For example, in entry 6, the yield is 33%. This probably is because of its volatility. In some examples, sulfuric acid is used. For example, in entry 7, 5 mol % of sulfuric acid is used, and the yield is 89%.

TABLE 1

Palladium-catalysed methoxycarbonylation of δ-lactone 1 to 2a: optimization of the reaction conditions.[a]

| Entry | Precatalyst (mol %) | Solvent | Acid (mol %) | CO (bar) | t (h) | Y[b] (%) |
|---|---|---|---|---|---|---|
| 1 | $PdCl_2$ (1) | toluene | PTSA (1) | 40 | 5 | 58 |
| 2 | $PdCl_2$ (1) | toluene | PTSA (5) | 40 | 5 | 83 |
| 3 | $PdCl_2$ (1) | toluene | PTSA (10) | 40 | 5 | 89 |
| 4 | $PdCl_2$ (1) | toluene | PTSA (15) | 40 | 5 | 90 |
| 5 | $PdCl_2$ (1) | toluene | MSA (5) | 40 | 5 | 84 |
| 6 | $PdCl_2$ (1) | toluene | HCl (5) | 40 | 5 | 33 |
| 7 | $PdCl_2$ (1) | toluene | $H_2SO_4$ (5) | 40 | 5 | 89 |
| 8 | $PdCl_2(CH_3CN)_2$ (1) | toluene | $H_2SO_4$ (5) | 40 | 5 | 88 |
| 9 | $Pd(dba)_2$ (1) | toluene | $H_2SO_4$ (5) | 40 | 5 | 16 |
| 10 | $Pd(OAc)_2$ (1) | toluene | $H_2SO_4$ (5) | 40 | 5 | 19 |
| 11 | $PdCl_2$ (1) | $CH_3CN$ | $H_2SO_4$ (5) | 40 | 5 | 37 |
| 12 | $PdCl_2$ (1) | THF | $H_2SO_4$ (5) | 40 | 5 | 45 |
| 13 | $PdCl_2$ (1) | MeOH | $H_2SO_4$ (5) | 40 | 5 | 39 |
| 14[c] | $PdCl_2$ (0.5) | toluene | $H_2SO_4$ (5) | 40 | 3 | 86 |
| 15 | $PdCl_2$ (0.5) | toluene | $H_2SO_4$ (5) | 40 | 3 | 89 |
| 16[d] | $PdCl_2$ (0.5) | toluene | $H_2SO_4$ (5) | 40 | 3 | 87 |
| 17 | $PdCl_2$ (0.5) | toluene | $H_2SO_4$ (5) | 30 | 3 | 89 |
| 18 | $PdCl_2$ (0.5) | toluene | $H_2SO_4$ (5) | 20 | 3 | 87 |
| 19[e] | $PdCl_2$ (0.5) | toluene | $H_2SO_4$ (7.5) | 30 | 3 | 91[f] |
| 20[g] | $PdCl_2$ (0.17) | toluene | $H_2SO_4$ (1.7) | 30 | 5 | 80 |

[a]Reactions conditions: 1 (1.0 mmol), [Pd] (x mol %), L15 (2x mol %), solvent (2 mL), MeOH (0.25 mL, 6 mmol), CO.
[b]Determined by GC analysis using hexadecane as the internal standard. Yield is given as sum of E and Z isomers. E/Z ratio ranges from 3.6 to 4.2.
[c]130° C.
[d]110° C.
[f]MeOH (0.50 mL, 12 mmol), isolated yield 90%.
[g]1 (3.0 mmol), MeOH (0.75 mL, 18 mmol).

The inventors recognized that the source of palladium may be crucial for the outcome of the reaction. In some embodiments, several commonly used palladium(0) and (II) precursors are used, for example, in entries 8-10, $[Pd(dba)_2]$, $Pd(OAc)_2$, and $PdCl_2(CH_3CN)_2$ are used instead of $PdCl_2$. The results are shown in Table 1. The presence of chloride ion may be helpful to ensure the formation of a sufficiently stable catalytically active species. In some embodiments, the reaction medium may include toluene, an aprotic polar solvent, or a protic polar solvent. In some embodiments, the temperature of the reaction may be between 110° C. and 130° C. In some embodiments, the CO pressure may be between 20 and 40 bar.

In some embodiments, increasing the amounts of both sulfuric acid and methanol can result in a 91% yield. In some examples, such as in entry 20, the amounts of lactone and MeOH are increased, a good catalyst activity can still be achieved at 0.17 mol % loading.

In some embodiments, different alcohols are used. Some examples are shown in Table 2. In some embodiments, primary aliphatic alcohols are used, giving yields of 90% or greater, such as in entries 1-2. Notably, the alcohol most frequently used in plasticizers production, 2-ethylhexanol, gave the diester 2c in essentially quantitative yield. In some embodiments, benzyl and isopropyl alcohol are used providing the corresponding diesters (such as 2d and 2e in entries 3-4) in yields of 73% and 64%. However, tert-butanol and phenol did not afford the desired product at all (such as in entries 5-6). The lack of selectivity in these cases is not surprising considering that the first step of the process involves an alcoholysis reaction which often proceeds sluggishly with tertiary alcohols or phenols.

TABLE 2

Palladium-catalysed alkoxycarbonylation of δ-lactone 1 to 2 using different alcohols.[a]

| Entry | Alcohol | Acid (mol %) | Product | Yield (%)[b] |
|---|---|---|---|---|
| 1 | "BuOH | $H_2SO_4$ (5) | 2b | 90 (E/Z = 3.8) |
| 2 | 2-Ethylhexanol | $H_2SO_4$ (5) | 2c | 99 (E/Z = 4.2) |
| 3 | $PhCH_2OH$ | PTSA (10) | 2d | 73 (E/Z = 4.5) |
| 4 | $^iPrOH$ | $H_2SO_4$ (5) | 2e | 64 (E/Z = 2.3) |
| 5 | $^tBuOH$ | PTSA (10) | 2f | — |
| 6 | PhOH | PTSA (10) | 2g | — |

[a]Reactions conditions: 1 (1.0 mmol), [Pd] (0.5 mol %), L15 (1 mol %), ROH (6 mmol), 30 bar CO in toluene (2 mL) for 5h.
[b]Determined by GC analysis using hexadecane as the internal standard. Yield is given as sum of E and Z isomers.

In some embodiments, alkoxycarbonylation on 1-3 mmol scale is performed in a 4 mL vial placed inside a 300 mL stainless steel Parr autoclave. Molar ratios and experimental conditions used in some embodiments are shown in Scheme 8, Table 1, and Table 2. In some embodiments, palladium precursor (0.01 mmol, 1 mol %), ligand (0.02 mmol, 2 mol %), δ-lactone (152 mg, 1.0 mmol) and a magnetic stirring bar are placed in a 4 mL vial. In some embodiments, when catalyst loading is lower than 1 mol %, a stock solution of $PdCl_2$ and L15 is prepared by mixing them in toluene and stirring the mixture overnight. In some embodiments, the vial is then sealed, connected to the atmosphere with a needle and evacuated and refilled with argon for three times. In some embodiments, solvent (for example, 2.0 mL) and a solution of the acidic promoter in the appropriate alcohol, are injected into the vial by syringe. In some embodiments where phenol and tert-butanol are used, the alcohol and the acid are added by weight. In some embodiments, the autoclave is flushed three times with CO, pressurised to the required pressure, and then placed in a preheated aluminium block. In some embodiments, after the reaction time, the autoclave is cooled with ice water to room temperature, and the pressure was carefully released. In some embodiments, the reaction mixture is analysed by gas-chromatography using hexadecane as the internal standard. In some embodiments, the resultant products are isolated from the reaction mixture by column chromatography and analyzed.

In some embodiments, the reaction is performed in a Hastelloy-C 100 mL Parr autoclave. $PdCl_2$ (16.1 mg, $9.1 \times 10^{-2}$ mmol), L15 (215 mg, 0.18 mmol) and δ-lactone (9.11 g, 60 mmol) are weighed in a Schlenk flask. In some embodiments, the flask is purged with argon. In some embodiments, toluene (40 mL) and a solution of $H_2SO_4$ (95 mg) in MeOH (15 mL) are added. In some embodiments, the mixture is stirred for 1 h under argon and then transferred to the autoclave previously purged with argon. In some embodiments, the autoclave is flushed three times with CO, pressurised to 50 bar and then the heated to 120° C. for 7 h. In some embodiments, the autoclave is then cooled with ice water and vented. In some embodiments, the volatiles are evaporated under rotary evaporation and the crude was distilled under vacuum (0.25-0.20 mbar) collecting the fraction between 80-85° C. In some embodiments, purity is checked by gas-chromatography. In some embodiments, 2a is obtained in 81% yield.

In some embodiments, the commercial reagents are from Alfa Aesar, Aldrich, TCI or Strem. Unless otherwise stated, commercial reagents are used without purification. In some embodiments, δ-lactone is synthesised as previously reported and kept under Ar atmosphere after distillation. In some embodiments, PTSA is used as monohydrate. In some embodiments, Pd/C 10 wt % is from Aldrich (product n. 205699). In some embodiments, [Ru(Triphos)(TMM)] is synthesized as previously reported in the literature. In some embodiments, toluene, THF and methanol are collected from The Solvent Purification System by M BRAUN is used under standard Schlenk technique. In some embodiments, acetonitrile, n-butanol, 2-ethylhexanol, benzyl alcohol and i-propanol are dried using standard techniques and kept under Ar atmosphere. Analytical data of literature known compounds are in accord with reported data. In some embodiments, NMR spectra are recorded on Bruker AV-300, Bruker Fourier 300 or Bruker AV-400 NMR spectrometers. Multiplets are assigned as s (singlet), d (doublet), t (triplet), dd (doublet of doublet), m (multiplet) and br. s (broad singlet). FIGS. 3-8 show the NMR data of the resultant diesters from δ-lactone 1.

In some embodiments, measurements are carried out at room temperature. In some embodiments, mass spectra are recorded on an Agilent 6890/5973 GC-MS. In some embodiments, high resolution mass spectra (HRMS) are recorded on Agilent 6210 Time-of-Flight LC/MS (Agilent) with electrospray ionization (ESI). The data are given as mass units per charge (m/z) and intensities of signals are given in brackets. In some embodiments, for gas-chromatography (GC) analyses, Agilent HP-7890A chromatograph equipped with a FID instrument and a HP-5 column (polydimethylsiloxane with 5% phenyl groups, 30 m, 0.32 mm i.d., 0.25 μm film thickness) is used. In some embodiments, the products are isolated from the reaction mixture by column chromatography on silica gel 60, 0.063-0.2 mm, (Merck) using gradient elution from heptane to heptane/AcOEt=8:2.

In some embodiments, GC analyses are performed according to Table 3 using the following methods: oven temperature program: 50° C.; 15° C./min to 260° C., 6 min; injection volume 1 μL with a split of 50:1; and inlet temperature 200° C.

TABLE 3

| Entry | Compound | RetTime (min) |
|---|---|---|
| 1 | ![structure] | 11.20 |
| 2 | ![structure] | 10.68 |
| 3 | ![structure] | 10.31 |

In some embodiments, the scalability of the process is demonstrated. In some embodiments, a multi-gram scale methoxycarbonylation of 2a (Scheme 10) is performed. For example, using a low catalyst loading ($PdCl_2$=0.15 mol %, L15=0.3 mol %) and the concentrations of the other reagents used in entry 22, Table 1, 81% isolated yield of dimethyl 7-ethylideneoct-3-enedioate 2a was obtained.

Scheme 10: Multi-gram scale synthesis of 2a from δ-lactone 1

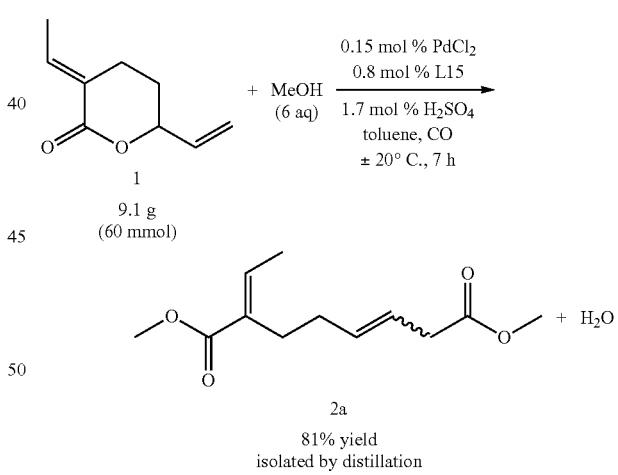

Unsaturated esters obtained by alkoxycarbonylation of δ-lactone 1 are valuable platform chemicals, and the corresponding saturated esters and the resultant diols are also of interest for a variety of different applications according to an embodiment.

In order to transform unsaturated diesters 2 of δ-lactone into saturated esters or diols, catalytic hydrogenations are performed. In some embodiments, commercial Pd/C (10 wt %) is used as catalyst to hydrogenate the unsaturated diester 2a. In some embodiments, mild reaction conditions (10 bar Hz, 60° C.) for the reduction of δ-lactone 1 to 3,6-diethyltetrahydro-2H-pyran-2-one, are used.

Scheme 11: Hydrogenation of diester 2a

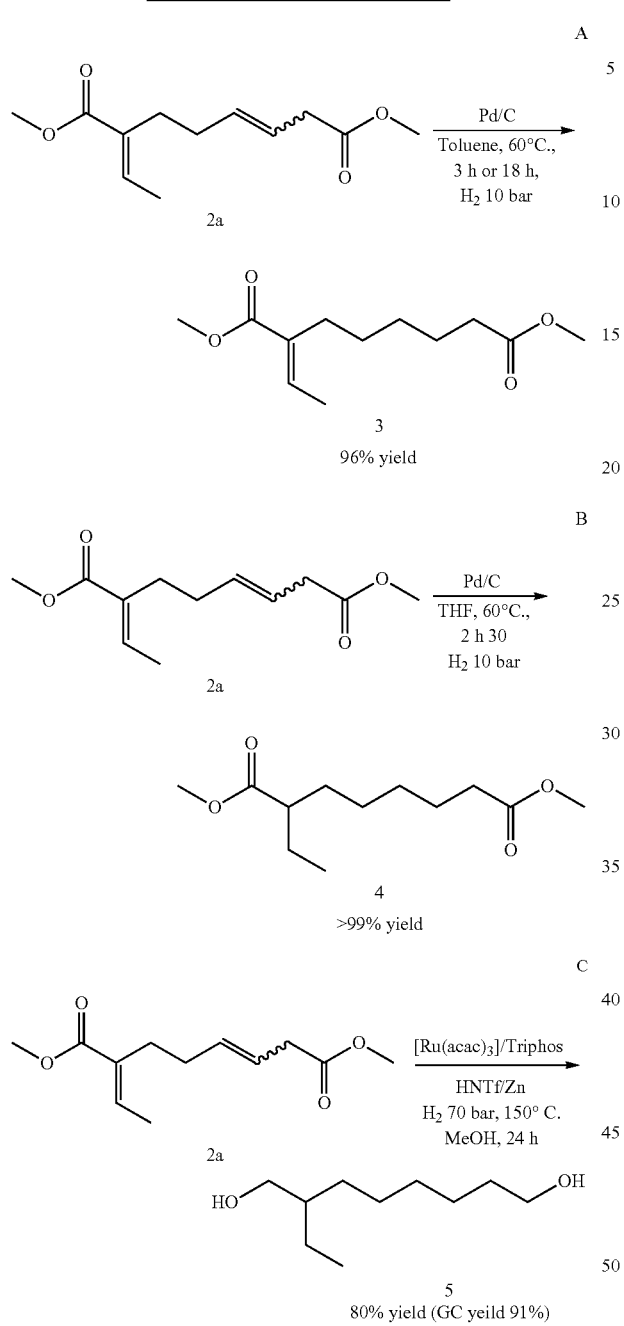

In some embodiments, diesters such as dimethyl 7-ethylideneoct-3-enedioate 2a derived from δ-lactone 1 can be chemo-selectively hydrogenated in toluene in high yields to produce partially hydrogenated to diesters 3 with the retention of a double bonds at C-2 carbon (Scheme 11A).

In some embodiments, Pd/C 10 wt % (2.8 mg), dimethyl 7-ethylideneoct-3-enedioate 2a (113 mg 0.5 mmol) and a magnetic stirring bar were added to a 4 mL vial. In some embodiments, the vial is then sealed with Septa (PTFE-faced styrene-butadiene rubber) and phenolic cap. In some embodiments, the vial is connected to the atmosphere with a needle. In some embodiments, the vial is evacuated and refilled with argon for three times. In some embodiments, toluene (2.0 mL) is injected into the vial by syringe. In some embodiments, the vial is placed inside a 300 mL stainless steel Parr autoclave. In some embodiments, the autoclave is flushed three times with nitrogen, pressurised with hydrogen to 10 bar and then heated to 60° C. for 3 h. In some embodiments, the autoclave is cooled with an ice bath and vented. In some embodiments, complete conversion is checked by GC analysis. In some embodiments, the reaction mixture is filtered through Celite, the solvent evaporated and the crude purified by column chromatography (gradient elution from heptane to heptane/AcOEt=8:2) affording (E)-dimethyl 2-ethylideneoctanedioate 3 as a colorless liquid in 96% yield.

The partially hydrogenated diesters 3 can be considered as analogues of acrylates (Scheme 12). Examples of such polymerization processes include the synthesis of long and short chain polymerization products using Chain Transfer Polymeraion (CTP), controlled radical polymerization such as ATRP, RAFT, and NMP methodologies.

Scheme 12: Radical polymerization of acrylates

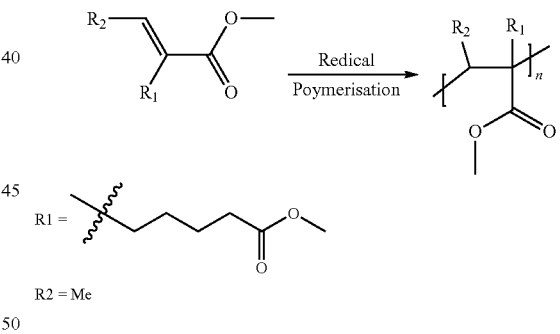

The diester 3 may also be used as a co-monomer for the co-polymerization processes using ethylene, propylene or alpha-olefins (Scheme 13).

Scheme 13: Co-polymerisation processes using ethylene, propylene or alpha-olefins

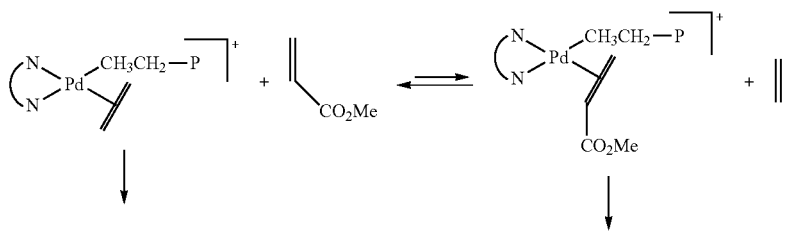

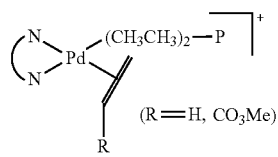
(R=H, CO₃Me)

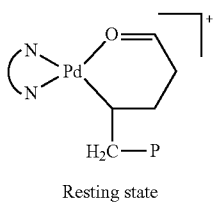
Resting state

The diester 3 may also be used as a feedstock for the metathesis reactions to produce polyesters and polyols (Scheme 14).

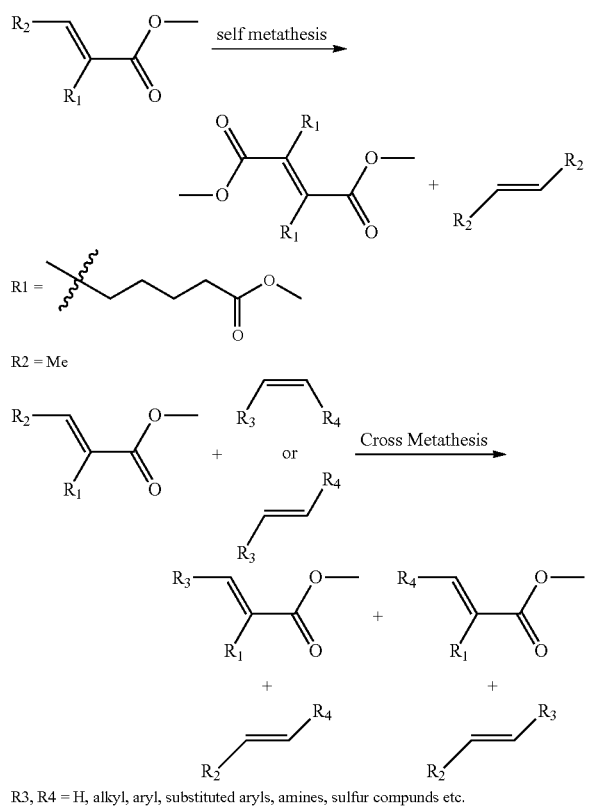

R3, R4 = H, alkyl, aryl, substituted aryls, amines, sulfur compunds etc.

In some embodiments, diesters such as dimethyl 7-ethylideneoct-3-enedioate 2a derived from δ-lactone 1 can be chemo-selectively hydrogenated in THF in high yields to produce fully hydrogenated to diesters 4 (Scheme 11B).

In some embodiments, Pd/C 10 wt % (3.1 mg), dimethyl 7-ethylideneoct-3-enedioate 2a (1.4 mmol) and a magnetic stirring bar were added to a 4 mL vial. In some embodiments, the vial is then sealed with Septa (PTFE-faced styrene-butadiene rubber) and phenolic cap. In some embodiments, the vial is connected to the atmosphere with a needle. In some embodiments, the vial is evacuated and refilled with argon for three times. In some embodiments, THF (3 mL) is added and the vial placed inside a 300 mL stainless steel Parr autoclave. In some embodiments, the autoclave is flushed three times with nitrogen, pressurised with hydrogen to 10 bar and then heated to 60° C. for 2.5 h. In some embodiments, the autoclave is cooled with an ice bath and vented. In some embodiments, complete conversion is checked by GC analysis. In some embodiments, the reaction mixture is filtered through Celite and the solvent evaporated affording pure dimethyl 2-ethyloctanedioate 4 as a colorless liquid in >99% yield.

The inventors noticed a marked solvent effect on the chemoselectivity of the hydrogenation. In some embodiments, the reaction is performed in toluene, and reduction of the di-substituted double bond is attained within 3 h. However, the conjugated tri-substituted double bond is not reduced even after 16 h, such as in Scheme 11A. In some embodiments, complete reduction of olefinic bonds of 2a to yield 4 is accomplished in 2.5 h using THF as the solvent, such as in Scheme 11B. The diester 4 is of potential industrial interest for plasticizer applications and as co-monomer in combination with diamines and diols to yield respectively polyamides and polyesters. On the other hand, the presence of a single unsaturation makes 3 comparable to α,β-unsaturated esters, e.g. acrylic and tiglic acid derivatives which are of interest for the preparation of different functional materials.

To further illustrate the versatility of 2 as building blocks for polymers, the inventors studied its hydrogenation to diol 5 (Scheme 11C). Conventionally, synthesis of diol 5 can be performed by reduction of 4 using $LiAlH_4$ as stoichiometric reagent. However, using this conventional reaction, the separation and purification of 5 from byproducts is difficult. Such methodology is clearly not environmental compatible and nowadays not applicable to a bulk scale industrial production. On the other hand, ester and carboxylic acid moieties are challenging functional groups for hydrogenation reactions. In industrial processes, their hydrogenation is generally performed over heterogeneous catalysts at high pressures and temperatures. The inventors investigated homogenous catalyzed hydrogenation of dimethyl 7-ethylideneoct-3-enedioate 2a, which can be used a valuable platform chemical for diols for application in polymer industry either as a feedstock for polymer production or as plasticiser alcohols.

In some embodiments, two different commercially available ruthenium based catalysts are used in the reduction of 2a to 5. A Noyori type ruthenium catalyst for the hydrogenation of esters (c1, Table 3) and the tetrahydroborato form of the ruthenium PNP pincer complex named Ru-MACHO™ (c2, Table 3) are used in entries 1 and 2. Unfortunately, even after 22 hours, only traces of diol were present using c1 as the catalyst and just 8% yield was obtained using c2.

However, promising results can be obtained using ruthenium complexes of 1,1,1-tris-(diphenylphsphinomethyl)etane (Triphos). The effect of water, MSA and zinc and solvent in the reduction of natural oil-derived diester was studied. In addition, a strong dependence of the selectivity for biogenic acid reduction upon change of ionic or acid additives was also studied. [Ru(Triphos)(TMM)] c3

(TMM=trimethylenemethane) and the in situ formed system from [Ru(acac)$_3$]/Triphos (c4 in Table 3, acac= acetylacetonate) were investigated, and interestingly, it was found out that the addition of acid additives lowers the selectivity towards benzyl alcohol in the hydrogenation of benzoic acid. The use of Lewis acids as promoters in the reductive etherification of esters was also studied.

tive. In some embodiments, the use of HNTf$_2$ (10 mol %) afforded 69% yield of 5 (entry 5, Table 4). In some embodiments, the desired full reduction of 2a to diol 5 is obtained under relatively mild conditions in 91% yield (80% isolated) upon reduction of the amount of HNTf$_2$ to 5 mol % and addition of 5 mol % of metallic zinc, for example, in entry 7, Table 4.

TABLE 4

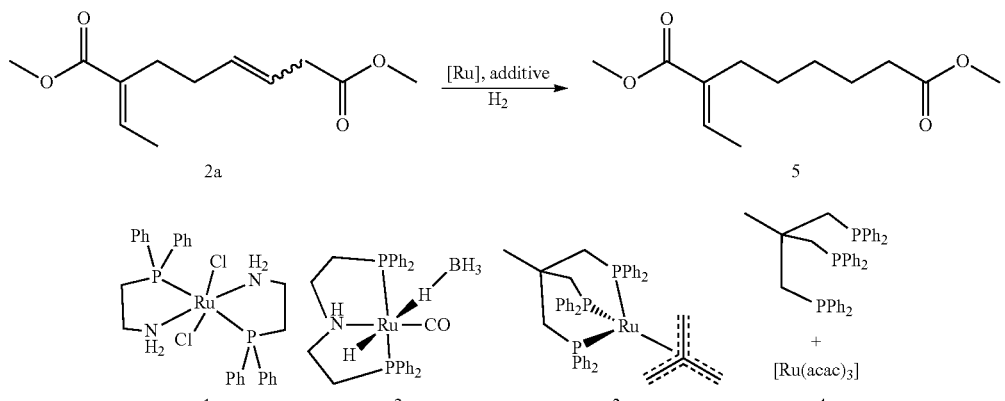

| Entry | Catalyst | Solvent | Additive (mol %) | CO (bar) | T (° C.) | t (h) | 6 Yield (%) |
|---|---|---|---|---|---|---|---|
| 1 | c1 | THF | MeONa (10) | 50 | 120 | 22 | traces |
| 2 | c2 | THF | — | 50 | 120 | 22 | 8 |
| 3 | c3 | THF | — | 70 | 150 | 22 | 2 |
| 4 | c4 | MeOH | MSA (10) | 70 | 150 | 22 | 35 |
| 5 | c4 | MeOH | HNTf$_2$ (10) | 70 | 150 | 22 | 69 |
| 6 | c4 | MeOH | MSA (5)/Zn (5) | 70 | 150 | 24 | 42 |
| 7 | c4 | MeOH | HNTf$_2$ (5)/Zn (5) | 70 | 150 | 24 | 91 |
| 8 | c4 | MeOH | MeONa (10) | 70 | 150 | 22 | 17 |
| 9 | c4 | dioxane | HNTf$_2$ (5) | 70 | 150 | 22 | 24 |

$^a$Reactions conditions: 3 (0.5 mmol), metal complex (0.01 mmol), ligand when added (0.02 mmol), solvent (2 mL).
Conversion of 3 was complete in all cases.
Yields were determined by GC analysis using hexadecane as internal standard.
MSA = methanesulfonic acid.
HNTf$_2$ = bis(trifluoromethane)sulfonimide.

In some embodiments, metal complex or catalyst precursor and ligand, for example, [Ru(acac)$_3$] (for example, 4.0 mg, 0.01 mmol), Triphos (for example, 12.5 mg, 0.02 mmol) and zinc (for example, 1.6 mg, 2.5×10$^{-2}$ mmol), are quickly weighed in a 4 mL vial in the air. In some embodiments, the vial is then sealed, connected to the atmosphere with a needle and evacuated and refilled with argon for three times. In some embodiments, 2a (for example, 0.5 mmol) and a stock solution of the solvent containing the appropriate additive, for example, HNTf$_2$ (7.0 mg, 2.5×10$^{-2}$ mmol) in methanol, are added. In some embodiments, the vial is placed inside a 300 mL stainless steel Parr autoclave, and the autoclave is flushed three times with nitrogen, pressurized with hydrogen and heated. In some embodiments, after the reaction time, the autoclave is cooled with ice water and vented. In some embodiments, the crude is analyzed by gas-chromatography. In some embodiments, isolated yield is obtained by purification on silica gel (gradient elution from CH$_2$Cl$_2$ to CH$_2$Cl$_2$/MeOH 9:1).

In some embodiments, c4 in combination with MSA in methanol (entry 4, Table 4) is used. In comparison, c3 in THF in absence of any additive (entry 3, Table 4) is used. The former yielded 35% of diol 5 while the latter afforded mainly a mixture of the esters 3 and 4. In some embodiments, sodium methoxide is used as the solvent, and bis (trifluoromethane)sulfonimide (HNTf$_2$) is used as an addi- The reactions of the entries in Table 4 are described in detail as follows:

Entry 1: A 4 mL vial was charged with c 1 (6.0 mg, 0.01 mmol) and a magnetic stirring bar. The vial was placed in a Schlenk tube evacuated and refilled with argon for three times and CH$_3$ONa (2.6 mg, 0.05 mmol, 10 mol %) was then added. The vial was then sealed with Septa (PTFE-faced styrene-butadiene rubber) and phenolic cap. The vial was connected to an argon line with a needle. 3 (113 mg, 0.5 mmol) and THF (2.0 mL), were injected into the vial by syringe. The vial was placed in an alloy plate, which was transferred into an autoclave (300 mL) of the 4760 series from Parr Instruments under argon atmosphere. After flushing the autoclave three times with nitrogen, the pressure of hydrogen was increased to 50 bar at room temperature. The reaction was performed for 22 h at 120° C. After the reaction time, the autoclave was cooled to room temperature and the pressure was carefully released. Then hexadecane (0.100 mL,) was injected as the internal standard. Yield was measured by GC analysis.

Entry 2: A 4 mL vial was charged with c2 (5.4 mg, 0.01 mmol) and a magnetic stirring bar. The vial was then sealed with Septa (PTFE-faced styrene-butadiene rubber) and phenolic cap. The vial was connected to the atmosphere with a needle. The vial was evacuated and refilled with argon for three times. 3 (113 mg, 0.5 mmol) and THF (2.0 mL), were injected into the vial by syringe. The vial was placed in an alloy plate, which was transferred into an autoclave (300 mL) of the 4760 series from Parr Instruments under argon atmosphere. After flushing the autoclave three times with nitrogen, the pressure of hydrogen was increased to 50 bar at room temperature. The reaction was performed for 22 h at 120° C. After the reaction time, the autoclave was cooled to room temperature and the pressure was carefully released. Then hexadecane (0.100 mL,) was injected as the internal standard. Yield was measured by GC analysis.

Entry 3: A 4 mL vial was charged with c3 (7.8 mg, 0.01 mmol), and a magnetic stirring bar. The vial was then sealed with Septa (PTFE-faced styrene-butadiene rubber) and phenolic cap. The vial was connected to the atmosphere with a needle. The vial was evacuated and refilled with argon for three times. 3 (113 mg, 0.5 mmol) and THF (2.0 mL), were injected into the vial by syringe. The vial was placed in an alloy plate, which was transferred into an autoclave (300 mL) of the 4760 series from Parr Instruments under argon atmosphere. After flushing the autoclave three times with nitrogen, the pressure of hydrogen was increased to 70 bar at room temperature. The reaction was performed for 22 h at 150° C. After the reaction time, the autoclave was cooled to room temperature and the pressure was carefully released. Then hexadecane (0.100 mL,) was injected as the internal standard. Yield was measured by GC analysis.

Entry 4: A 4 mL vial was charged with Ru(acac)$_3$ (4.0 mg, 0.01 mmol), 1,1,1-tris(diphenylphosphinomethyl)ethane (11.5 mg, 0.02 mmol) and a magnetic stirring bar. The vial was then sealed with Septa (PTFE-faced styrene-butadiene rubber) and phenolic cap. The vial was connected to the atmosphere with a needle. The vial was evacuated and refilled with argon for three times. 3 (113 mg, 0.5 mmol), a 0.05M methanesulfonic acid solution in MeOH (1.0 mL, 10 mol %) and MeOH (1.0 mL), were injected into the vial by syringe. The vial was placed in an alloy plate, which was transferred into an autoclave (300 mL) of the 4760 series from Parr Instruments under argon atmosphere. After flushing the autoclave three times with nitrogen, the pressure of hydrogen was increased to 70 bar at room temperature. The reaction was performed for 22 h at 150° C. After the reaction time, the autoclave was cooled to room temperature and the pressure was carefully released. Then hexadecane (0.100 mL,) was injected as the internal standard. Yield was measured by GC analysis.

Entry 5: A 4 mL vial was charged with Ru(acac)$_3$ (4.0 mg, 0.01 mmol), 1,1,1-tris(diphenylphosphinomethyl)ethane (11.5 mg, 0.02 mmol) and a magnetic stirring bar. The vial was then sealed with Septa (PTFE-faced styrene-butadiene rubber) and phenolic cap. The vial was connected to the atmosphere with a needle. The vial was evacuated and refilled with argon for three times. 3 (113 mg, 0.5 mmol), a 0.05M HNTf$_2$ solution in MeOH (1.0 mL, 10 mol %) and MeOH (1.0 mL), were injected into the vial by syringe. The vial was placed in an alloy plate, which was transferred into an autoclave (300 mL) of the 4760 series from Parr Instruments under argon atmosphere. After flushing the autoclave three times with nitrogen, the pressure of hydrogen was increased to 70 bar at room temperature. The reaction was performed for 22 h at 150° C. After the reaction time, the autoclave was cooled to room temperature and the pressure was carefully released. Then hexadecane (0.100 mL,) was injected as the internal standard. Yield was measured by GC analysis.

Entry 6: A 4 mL vial was charged with Ru(acac)$_3$ (4.0 mg, 0.01 mmol), 1,1,1-tris(diphenylphosphinomethyl)ethane (11.5 mg, 0.02 mmol), metallic zinc powder (1.7 mg, 0.025 mmol, 5 mol %) and a magnetic stirring bar. The vial was then sealed with Septa (PTFE-faced styrene-butadiene rubber) and phenolic cap. The vial was connected to the atmosphere with a needle. The vial was evacuated and refilled with argon for three times. 3 (113 mg, 0.5 mmol), a 0.54M methanesulfonic acid solution in MeOH (0.050 mL, 5 mol %) and MeOH (2.0 mL), were injected into the vial by syringe. The vial was placed in an alloy plate, which was transferred into an autoclave (300 mL) of the 4760 series from Parr Instruments under argon atmosphere. After flushing the autoclave three times with nitrogen, the pressure of hydrogen was increased to 70 bar at room temperature. The reaction was performed for 24 h at 150° C. After the reaction time, the autoclave was cooled to room temperature and the pressure was carefully released. Then hexadecane (0.100 mL,) was injected as the internal standard. Yield was measured by GC analysis.

Entry 7: A 4 mL vial was charged with Ru(acac)$_3$ (4.0 mg, 0.01 mmol), 1,1,1-tris(diphenylphosphinomethyl)ethane (11.5 mg, 0.02 mmol), metallic zinc powder (1.7 mg, 0.025 mmol, 5 mol %) and a magnetic stirring bar. The vial was then sealed with Septa (PTFE-faced styrene-butadiene rubber) and phenolic cap. The vial was connected to the atmosphere with a needle. The vial was evacuated and refilled with argon for three times. 3 (113 mg, 0.5 mmol), a 0.025M HNTf$_2$ solution in MeOH (1.0 mL, 5 mol %) and MeOH (1.0 mL), were injected into the vial by syringe. The vial was placed in an alloy plate, which was transferred into an autoclave (300 mL) of the 4760 series from Parr Instruments under argon atmosphere. After flushing the autoclave three times with nitrogen, the pressure of hydrogen was increased to 70 bar at room temperature. The reaction was performed for 24 h at 150° C. After the reaction time, the autoclave was cooled to room temperature and the pressure was carefully released. Then hexadecane (0.100 mL,) was injected as the internal standard. Yield was measured by GC analysis. The product was purified by column chromatography on silica gel (gradient elution from CH$_2$Cl$_2$ to CH$_2$Cl$_2$/MeOH 9:1).

Entry 8: A 4 mL vial was charged with Ru(acac)$_3$ (4.0 mg, 0.01 mmol), 1,1,1-tris(diphenylphosphinomethyl)ethane (11.5 mg, 0.02 mmol) and a magnetic stirring bar. The vial was then sealed with Septa (PTFE-faced styrene-butadiene rubber) and phenolic cap. The vial was connected to the atmosphere with a needle. The vial was evacuated and refilled with argon for three times. 3 (113 mg, 0.5 mmol), a 0.5M CH$_3$ONa solution in MeOH (1.0 mL, 10 mol %) and MeOH (1.0 mL), were injected into the vial by syringe. The vial was placed in an alloy plate, which was transferred into an autoclave (300 mL) of the 4760 series from Parr Instruments under argon atmosphere. After flushing the autoclave three times with nitrogen, the pressure of hydrogen was increased to 70 bar at room temperature. The reaction was performed for 22 h at 150° C. After the reaction time, the autoclave was cooled to room temperature and the pressure was carefully released. Then hexadecane (0.100 mL,) was injected as the internal standard. Yield was measured by GC analysis.

Entry 9: A 4 mL vial was charged with Ru(acac)$_3$ (4.0 mg, 0.01 mmol), 1,1,1-tris(diphenylphosphinomethyl)ethane (11.5 mg, 0.02 mmol) and a magnetic stirring bar. The vial was then sealed with Septa (PTFE-faced styrene-butadiene rubber) and phenolic cap. The vial was connected to the atmosphere with a needle. The vial was evacuated and refilled with argon for three times. 3 (113 mg, 0.5 mmol), a 0.025M HNTf$_2$ solution in dioxane (1.0 mL, 5 mol %) and dioxane (1.0 mL), were injected into the vial by syringe. The vial was placed in an alloy plate, which was transferred into an autoclave (300 mL) of the 4760 series from Parr Instruments under argon atmosphere. After flushing the autoclave three times with nitrogen, the pressure of hydrogen was increased to 70 bar at room temperature. The reaction was performed for 22 h at 150° C. After the reaction time, the autoclave was cooled to room temperature and the pressure was carefully released. Then hexadecane (0.100 mL,) was injected as the internal standard. Yield was measured by GC analysis.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A process of manufacturing a renewable feedstock for polymer production, the process comprising:
   preparing a $CO_2$ derived lactone; and
   processing the $CO_2$ derived lactone to form the renewable feedstock, wherein processing the $CO_2$ derived lactone comprises selectively hydrogenating the $CO_2$ derived lactone to form a hydrogenated $CO_2$ derived lactone.

2. The process of claim 1, wherein the hydrogenated $CO_2$ derived lactone is processed to form 2-ethylideneheptanoic acid using one or both of a homogeneous hydrogenation system and a heterogeneous hydrogenation system.

3. The process of claim 2, wherein the hydrogenated $CO_2$ derived lactone is processed according to a reaction as follows:

4. A process of manufacturing a renewable feedstock for polymer production, the process comprising:
   preparing a $CO_2$ derived lactone; and
   processing the $CO_2$ derived lactone to form the renewable feedstock, wherein processing the $CO_2$ derived lactone comprises selectively hydrogenating the $CO_2$ derived lactone to form a hydrogenated $CO_2$ derived lactone, and wherein the hydrogenated $CO_2$ derived lactone is processed using a Rh/phosphine biphasic hydrogenation system.

5. A process of manufacturing a renewable feedstock for polymer production, the process comprising:
   preparing a $CO_2$ derived lactone; and
   processing the $CO_2$ derived lactone to form the renewable feedstock, wherein processing the $CO_2$ derived lactone comprises selectively hydrogenating the $CO_2$ derived lactone to form a hydrogenated $CO_2$ derived lactone, and wherein the hydrogenated $CO_2$ derived lactone is processed by using a thiol click reaction to produce a regioselective polymer.

6. The process of claim 5, wherein the hydrogenated $CO_2$ derived lactone is processed according to a reaction as follows:

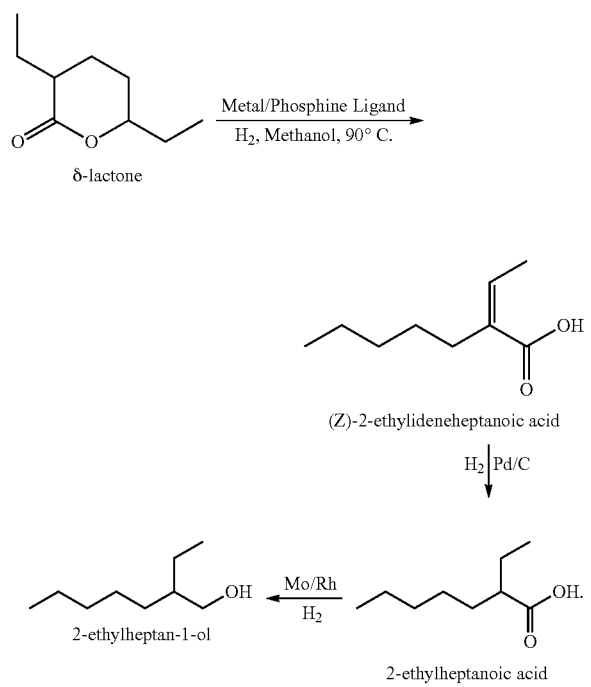

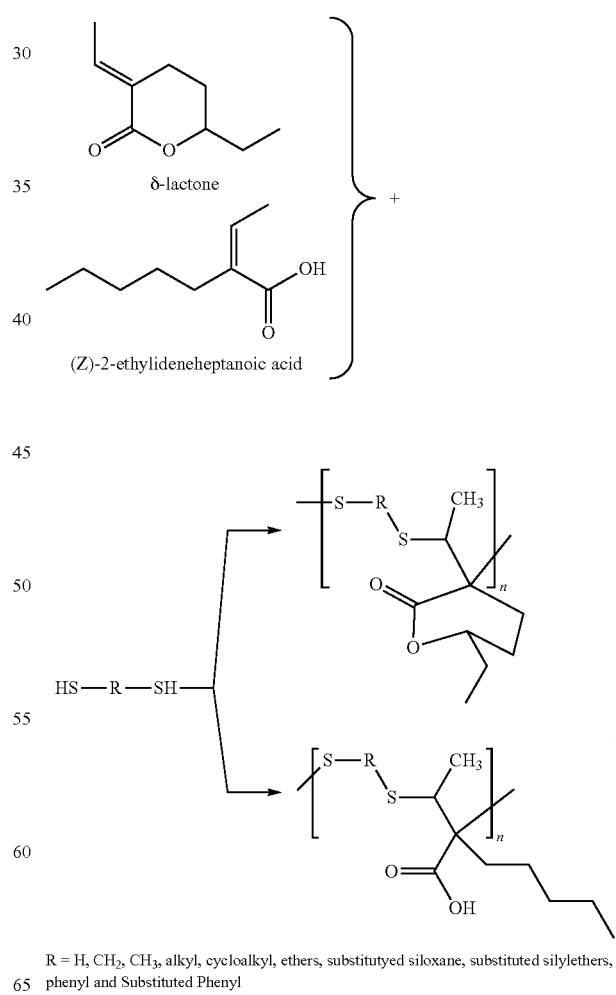

R = H, $CH_2$, $CH_3$, alkyl, cycloalkyl, ethers, substitutyed siloxane, substituted silylethers, phenyl and Substituted Phenyl 7. A process of manufacturing a renewable feedstock for polymer production, the process comprising:
preparing a $CO_2$ derived lactone; and
processing the $CO_2$ derived lactone to form the renewable feedstock, wherein processing the $CO_2$ derived lactone comprises selectively hydrogenating the $CO_2$ derived lactone to form a hydrogenated $CO_2$ derived lactone, and wherein the hydrogenated $CO_2$ derived lactone is processed using an alkene metathesis.

8. The process of claim 7, the alkene metathesis includes a self-metathesis reaction as follows:

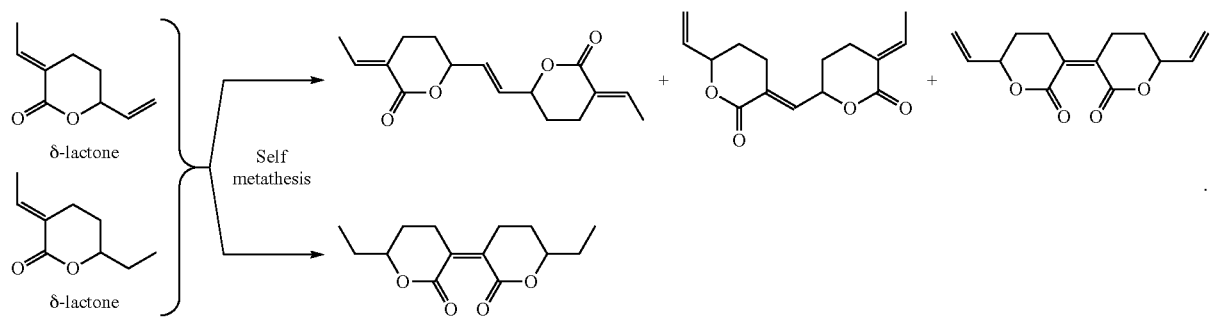 [SMILES: C=CC1CC/C(=C\C)C(=O)O1 ; C/C=C1\CCC(/C=C/C2CC/C(=C\C)C(=O)O2)OC1=O ; C=CC1CC/C(=C\C2CC/C(=C\C)C(=O)O2)C(=O)O1 ; C=CC1CC/C(=C2\CCC(C=C)OC2=O)C(=O)O1 ; C/C=C1\CCC(CC)OC1=O ; CCC1CC/C(=C2\CCC(CC)OC2=O)C(=O)O1]

9. The process of claim 7, wherein the alkene metathesis includes a cross metathesis as follows:

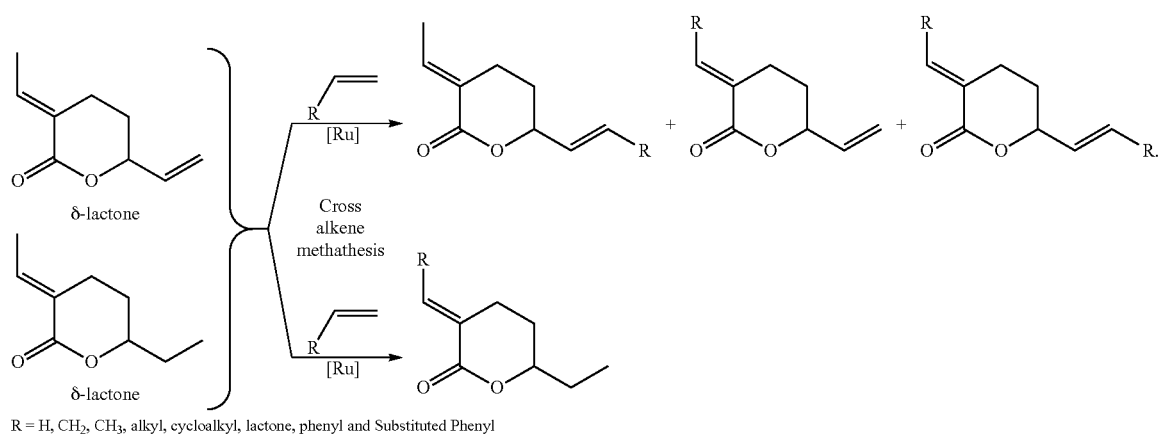

R = H, $CH_2$, $CH_3$, alkyl, cycloalkyl, lactone, phenyl and Substituted Phenyl 10. A process of manufacturing a renewable feedstock for polymer production, the process comprising:
preparing a $CO_2$ derived lactone;
processing the $CO_2$ derived lactone to form the renewable feedstock, wherein processing the $CO_2$ derived lactone comprises selectively hydrogenating the $CO_2$ derived lactone to form a hydrogenated $CO_2$ derived lactone; and
processing the hydrogenated $CO_2$ derived lactone, which includes a metal catalysed reaction as follows:

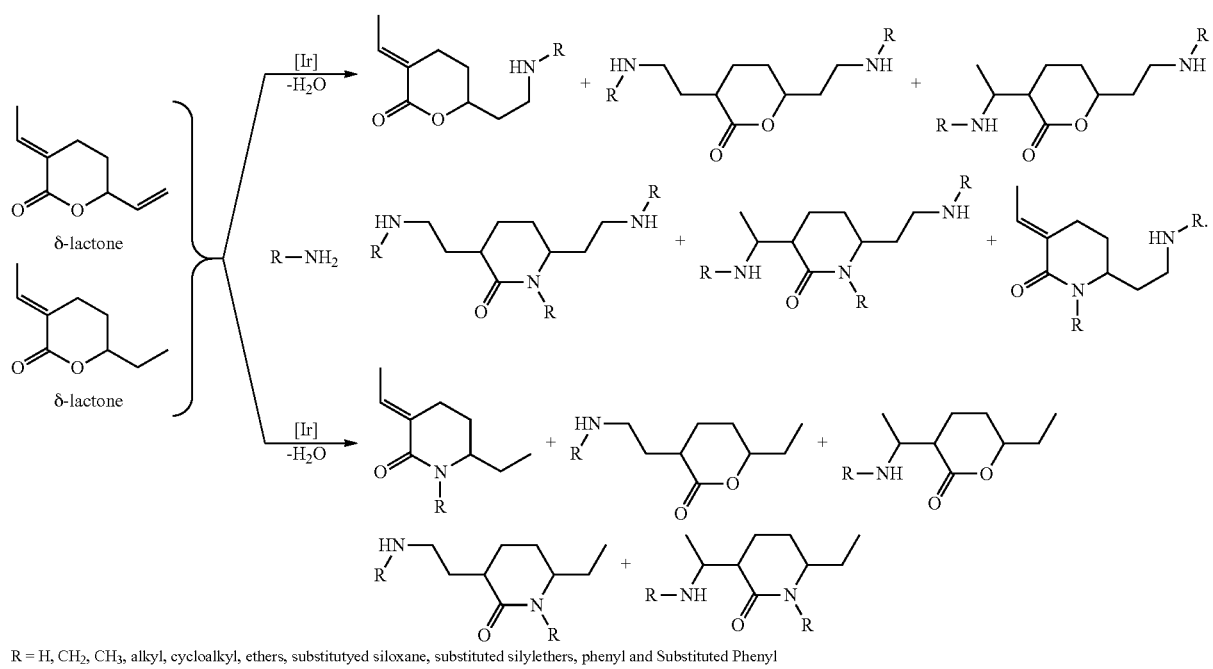

R = H, CH₂, CH₃, alkyl, cycloalkyl, ethers, substitutyed siloxane, substituted silylethers, phenyl and Substituted Phenyl 11. A process of manufacturing a renewable feedstock for polymer production, the process comprising:
    preparing a CO₂ derived lactone; and
    alkoxycarbonylating the CO₂ derived lactone to form a diester, wherein alkoxycarbonylating the CO₂ derived lactone includes a palladium compound catalyst, and wherein the palladium compound catalyst includes Pd(OAc), PdCl₂, or Pd(dba)₂.

12. The process of claim 11, further comprising hydrogenating the diester to form the renewable feedstock.

13. The process of claim 11, wherein alkoxycarbonylating the CO₂ derived lactone includes a methoxycarbonylation reaction as follows:

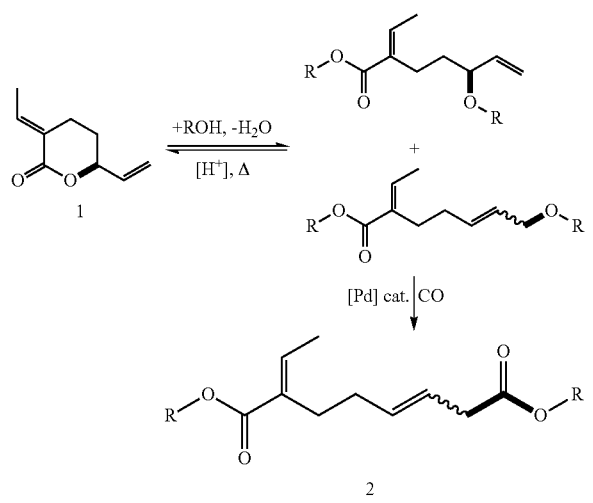

14. The process of claim 11, wherein alkoxycarbonylating includes a phosphine ligand.

15. The process of claim 11, wherein alkoxycarbonylating includes an alcohol.

16. The process of claim 11, wherein alkoxycarbonylating includes a solvent.

17. The process of claim 11, wherein alkoxycarbonylating includes an acid.

18. The process of claim 1, wherein the CO₂ derived lactone is selectively hydrogenated with 100% region-selective control for terminal carbon-carbon bonds.

19. The process of claim 1, wherein the CO₂ derived lactone is selectively hydrogenated to form the hydrogenated CO₂ derived lactone as follows:

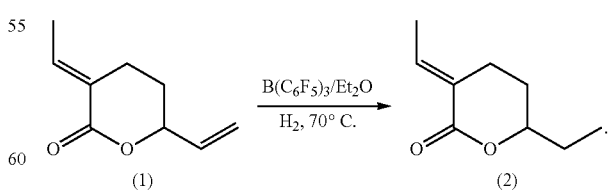

* * * * *